(12) United States Patent
Bodhuri et al.

(10) Patent No.: US 10,351,537 B2
(45) Date of Patent: Jul. 16, 2019

(54) PROCESSES FOR THE PREPARATION OF LESINURAD AND INTERMEDIATES THEREOF

(71) Applicant: Apotex Inc., Toronto (CA)

(72) Inventors: Prabhudas Bodhuri, Brantford (CA); Melanie R. A. Green, Milton (CA); Avedis Karadeolian, Cambridge (CA); Gamini Weeratunga, Ancaster (CA); Boris Gorin, Oakville (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 15/914,165

(22) Filed: Mar. 7, 2018

(65) Prior Publication Data

US 2018/0258057 A1    Sep. 13, 2018

Related U.S. Application Data

(60) Provisional application No. 62/469,656, filed on Mar. 10, 2017.

(51) Int. Cl.
   *C07D 249/12* (2006.01)

(52) U.S. Cl.
   CPC .................. *C07D 249/12* (2013.01)

(58) Field of Classification Search
   CPC .................................... C07D 249/12
   See application file for complete search history.

(56) References Cited

U.S. PATENT DOCUMENTS

| | | | |
|---|---|---|---|
| 8,003,681 B2 * | 8/2011 | Girardet | C07D 249/12 514/384 |
| 8,546,437 B2 | 10/2013 | Quart et al. | |
| 9,296,709 B2 | 3/2016 | Gunic et al. | |

FOREIGN PATENT DOCUMENTS

| | | |
|---|---|---|
| CN | 105017168 A | 11/2015 |
| CN | 105153056 A | 12/2015 |
| CN | 105566237 A | 5/2016 |
| WO | 2009070740 A2 | 6/2009 |
| WO | 2014008295 A1 | 1/2014 |
| WO | 2014198241 A1 | 12/2014 |
| WO | 2015054960 A1 | 4/2015 |

* cited by examiner

*Primary Examiner* — Laura L Stockton

(74) *Attorney, Agent, or Firm* — The Webb Law Firm

(57) ABSTRACT

The present invention provides processes for the preparation of Lesinurad (1), as well as intermediates useful in the preparation thereof. In particular, the processes of the invention utilize novel intermediate compounds of Formulas (3) and (11), which provide improvements over the known processes for the preparation of Lesinurad (1).

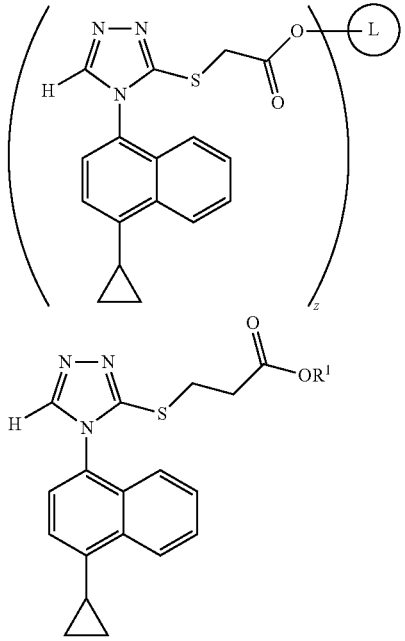

20 Claims, No Drawings

PROCESSES FOR THE PREPARATION OF LESINURAD AND INTERMEDIATES THEREOF

CROSS-REFERENCE TO RELATED APPLICATIONS

This application claims the benefit of U.S. Provisional Patent Application No. 62/469,656, filed Mar. 10, 2017, the disclosure of which is hereby incorporated in its entirety by reference.

TECHNICAL FIELD

The present invention relates to processes for the preparation of Lesinurad and intermediates used in the preparation thereof.

BACKGROUND

Lesinurad, or 2-((5-bromo-4-(4-cyclopropylnaphthalen-1-yl)-4H-1,2,4-triazol-3-yl)thio)acetic acid, is marketed in the United States as ZURAMPIC®, and is indicated, in combination with a xanthine oxidase inhibitor, for the treatment of hyperuricemia associated with gout in patients who have not achieved target serum uric acid levels with a xanthine oxidase inhibitor alone. Lesinurad has the following structural formula:

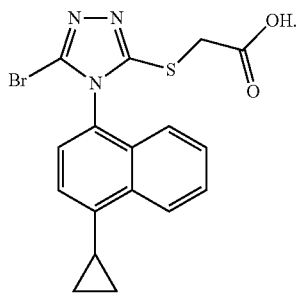

(1)

One method of preparing Lesinurad is described in WO 2009/070740 A2, which discloses a family of compounds that are useful in decreasing uric acid levels. Similar methods of preparing Lesinurad are disclosed in WO 2014/008295 A1 and CN 105566237 A. In this method, which is depicted in Scheme 1, Lesinurad is prepared from starting material (A) by reaction with a methyl haloacetate, followed by diazotization and displacement with bromide to yield the compound of Formula (C), which is further hydrolysed to yield Lesinurad (1).

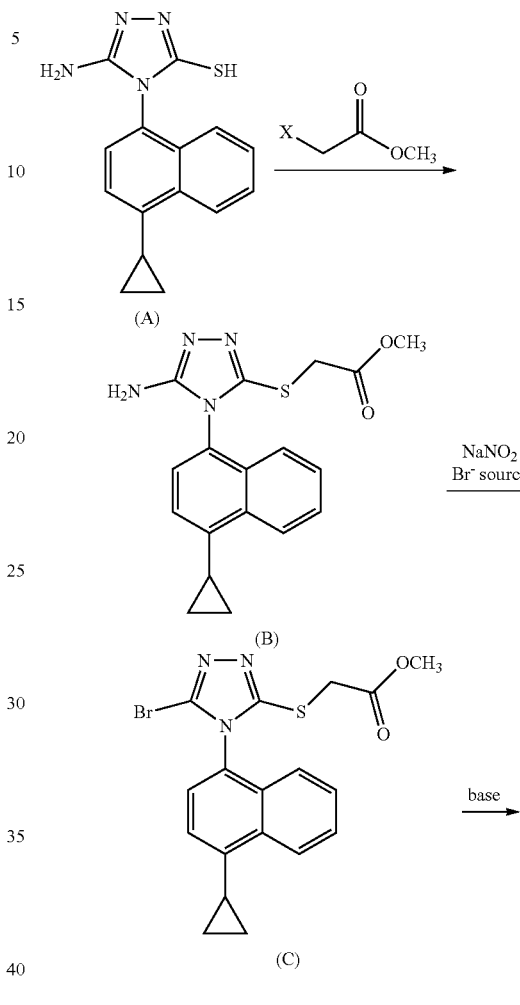

In WO 2009/070740 A2 and CN 105566237 A, bromination is conducted using excessive amounts of sodium nitrite, a strong oxidant, as well as a number of toxic and corrosive reagents, including tribromomethane and dichloroacetic acid. An alternative bromination is described in WO 2014/008295 A; however, the process uses equimolar amounts of cuprous bromide as the bromide source, which will result in higher costs when conducted on a commercial scale owing to the high cost of this reagent, as well as the waste disposal costs associated with the use of heavy metal reagents such as copper. Furthermore, the commercial application of this process is further hindered by the preparation of the compound of Formula (A), which is reported to be lengthy, requiring purification steps and multiple isolations of the same compound to produce the compound of Formula (A) having sufficient quality for use in the preparation of Lesinurad.

A second strategy for the preparation of Lesinurad is described in WO 2014/008295 A1 and WO 2015/054960 A1. In this approach, Lesinurad is prepared from starting material (D) by reaction with a methyl haloacetate followed by direct bromination of the triazole (E) to yield (C), which is hydrolyzed to provide Lesinurad (1) as shown in Scheme 2. A similar method for preparing Lesinurad is described in WO 2014/198241 A1, wherein analogues of triazole (E) having a variety of thioglycolate ester and amide sidechains are brominated.

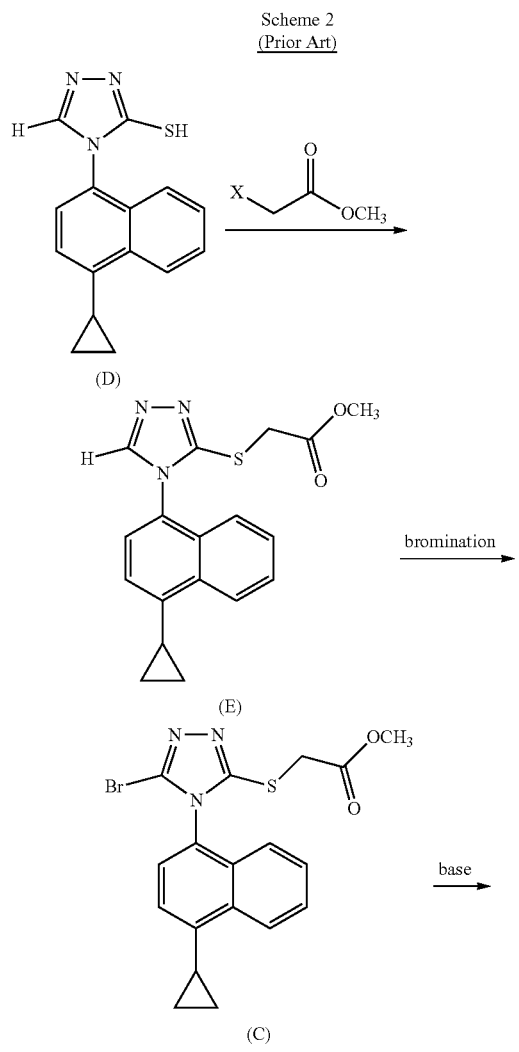

While this approach overcomes some of the problems associated with bromination of the compound of Formula (B), according to optimization results reported in WO 2014/008295 A1, the range of conditions available to achieve successful bromination in high purity is limited.

In alternative processes for the preparation of Lesinurad, such as those reported in CN 105017168 A and CN 105153056 A, installation of the thioglycolate side chain occurs by first displacing a hydroxyl or diazonium group (following diazotization of the amine) on the triazole ring of compounds (F) or (G), respectively, followed by addition of the thioglycolate side chain using methyl thioglycolate. However, methyl thioglycolate is a malodorous substance that is preferably avoided in processes conducted on an industrial scale.

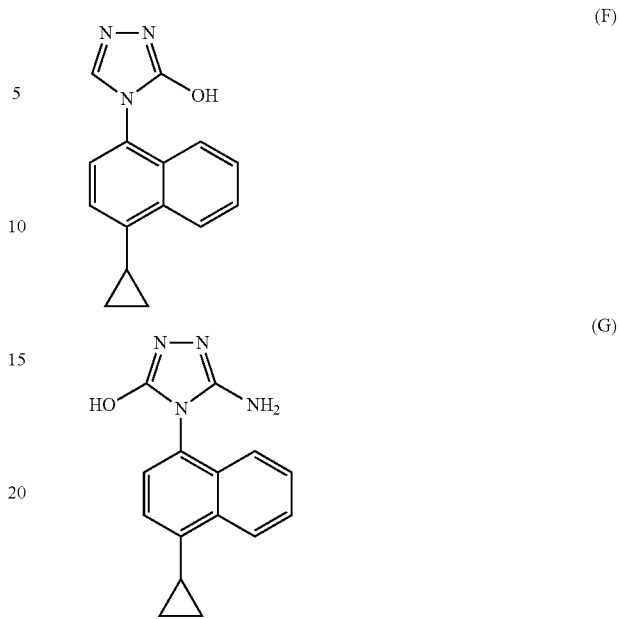

Many of the reported processes for the preparation of Lesinurad suffer from the use of toxic, corrosive, malodorous and/or expensive reagents, in some cases generating waste that requires special and costly disposal procedures. Additionally, the syntheses of some of the raw materials, such as the compound of Formula (A), are reported to be lengthy and complicated. These factors limit the practicality of using the known processes to prepare Lesinurad on a commercial scale. Owing to the drawbacks of the existing processes for the preparation of Lesinurad, there remains a need for improved processes for the preparation of Lesinurad, and the intermediates used in such preparations, that are more amenable to scale-up and use on a commercial scale.

SUMMARY OF THE INVENTION

The present invention provides improved processes for the preparation of Lesinurad (1), as well as new intermediates and processes for their preparation, as depicted in Scheme 3 and Scheme 4.

As shown in Scheme 3, Lesinurad may be prepared by bromination of a novel intermediate, the compound of Formula (3), which is formed by attaching two or more units of the compound of Formula (5) to the compound of Formula (4), the backbone of which is derived from either a monomeric polyol or a polymeric polyol (the compound of Formula (7)), followed by hydrolysis.

Scheme 3

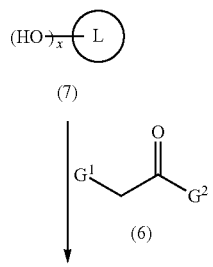

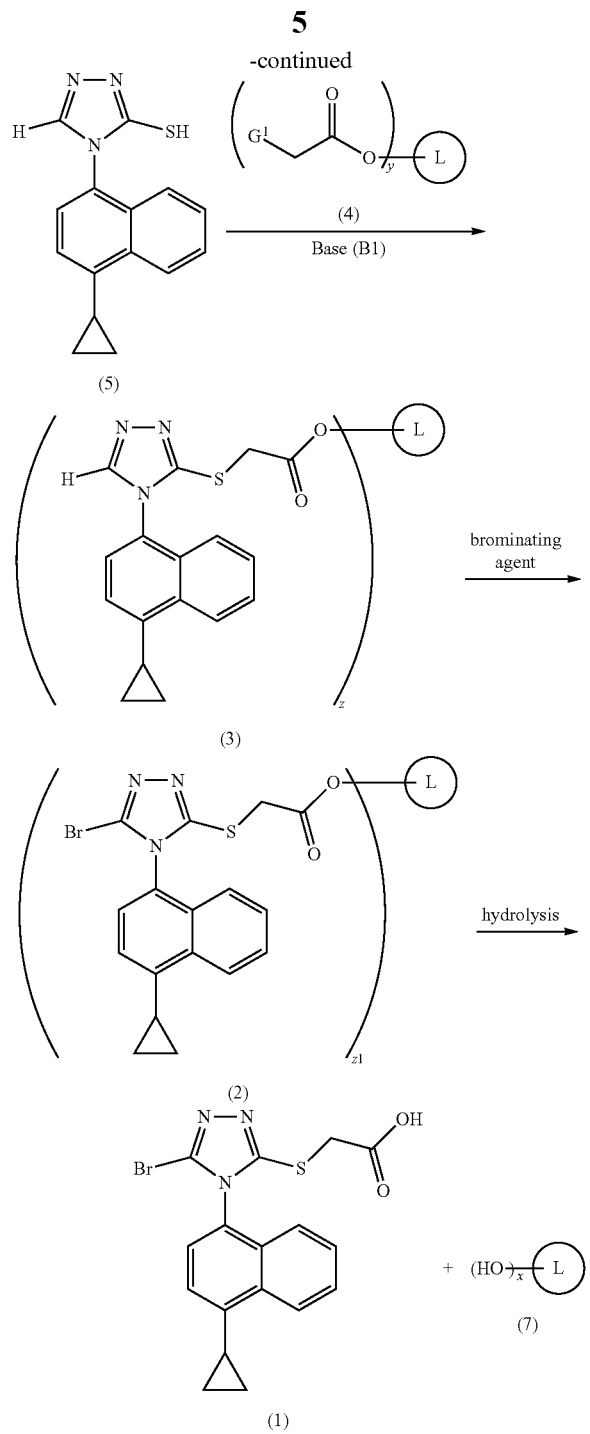

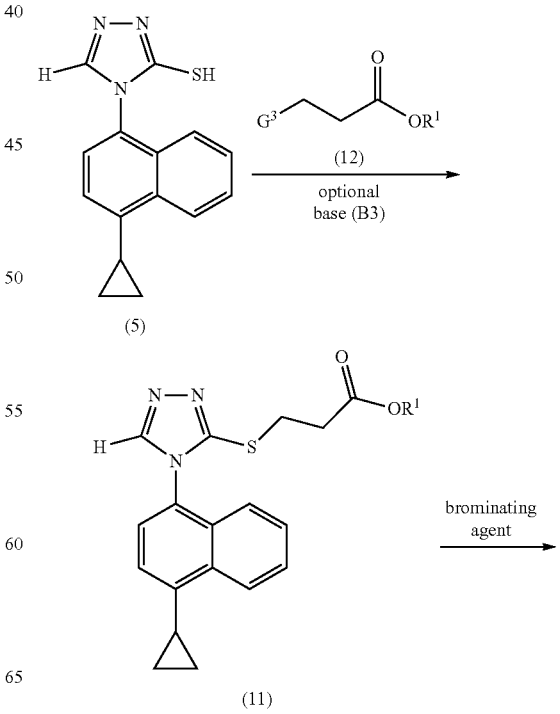

$G^1$ and $G^2$ are each independently a leaving group;

x, y, z, z and z1 are each at least 2; and z1≤z≤y≤x.

In certain embodiments of the processes of the invention, the polyol by-products released by hydrolysis following the bromination step are highly water-soluble, leading to simplification of the work-up steps, in particular, the biphasic separation and work-up procedures. Alternatively, in other embodiments of the process of the present invention, or the use of insoluble polymeric polyols, including hydroxyl-functionalized gel-type and modified surface-type polymers as a backbone provides the opportunity of using solid phase synthetic methods wherein the insoluble polyol is part of a solid resin or bead.

As shown in Scheme 4, in further embodiments of the invention, Lesinurad may be prepared by bromination of the compound of Formula (11), bearing a propanoate side chain for the bromination step that is then replaced with the ethanoate group of Lesinurad (1). In this process, it has surprisingly be found that the bromination of the compound of Formula (11), having an extended 3-carbon sidechain when compared to the shorter 2-carbon thioglycolate sidechain of Lesinurad (1), reduces the formation of impurities arising from the presence of a thio group in the alpha position relative to the carbonyl. When bromination of the compound of Formula (11) is conducted in the presence of an alpha thio group, such as in intermediate compounds (B) and (E) (see prior art Schemes 1 and 2), impurities arising from competing reactions at the alpha carbon have been identified. However, when the thio group is removed by one carbon in the compound of Formula (11), forming a beta-thio group relative to the carbonyl, the formation of these impurities is reduced.

wherein

L is a linker corresponding with the backbone of either:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom;
wherein the hydroxyl substituents of the polyol provide the oxygen atoms in the ester connection in the compounds of Formulas (2), (3) and (4);

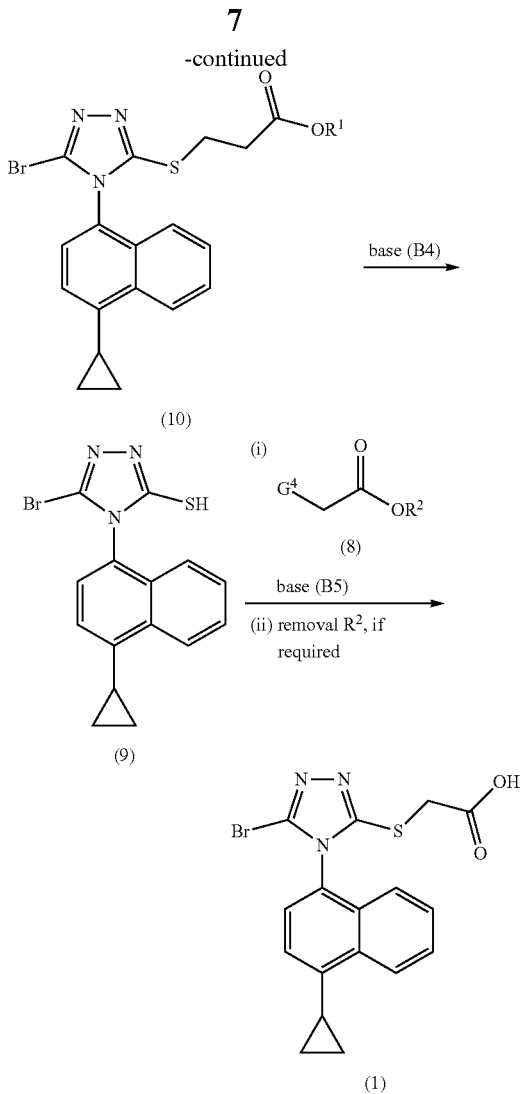

wherein
R[1] is selected from the group consisting of an aliphatic group, a substituted aliphatic group, aryl, substituted aryl, arylalkyl, substituted arylalkyl;
R[2] is H or R[1]; and
G[3] and G[4] are each independently a leaving group.

Accordingly, in a first aspect of the present invention, there is provided a process for the preparation of a compound of Formula (1):

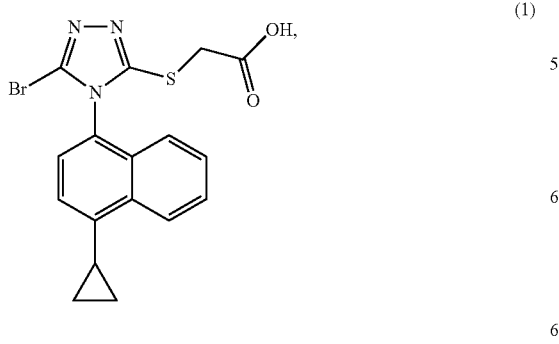

or a salt thereof, the process comprising hydrolysis, in the presence of a solvent (S3), of a compound of Formula (2):

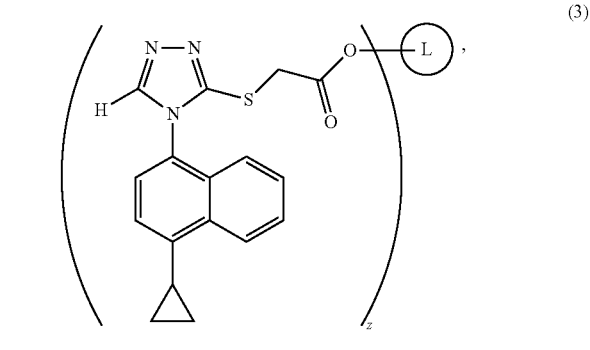

wherein
L is a linker corresponding with the backbone of either:
 (a) a monomeric polyol having x hydroxyl substituents, each bonded to a different carbon atom;
 (b) a water-soluble polymeric polyol having x mean hydroxyl substituents, each bonded to a different carbon atom; or
 (c) a water-insoluble polymeric polyol suitable for use as a solid phase support having x mean hydroxyl substituents, each bonded to a different carbon atom; and
wherein the hydroxyl substituents of the polyol provide the oxygen atoms in the ester connection in the compound of Formula (2);
x and z1 are each at least 2; and
z1≤x.

In a preferred embodiment of the first aspect, the hydrolysis of the compound of Formula (2) is conducted in the presence of base (B2). Preferably, base (B2) is an alkali metal hydroxide, and is most preferably lithium hydroxide. In another preferred embodiment of the first aspect, solvent (S3) is selected from the group consisting of water and ethers. Most preferably, solvent (S3) is tetrahydrofuran.

In another preferred embodiment of the first aspect, the compound of Formula (2) is prepared according to the process provided by the second aspect of the present invention, described below. Most preferably, when conducting the process of the invention according to this preferred embodiment, the compound of Formula (2) is not isolated between the processes of the first and second aspects of the invention.

In another preferred embodiment of the first aspect, the compound of Formula (2) is prepared by a process comprising reacting, in the presence of a solvent (S2), a compound of Formula (3):

with a brominating agent, wherein

L is a linker corresponding with the backbone of a monomeric polyol selected from the group consisting of ethane-1,2-diol and propane-1,2,3-triol; and z is 2 or 3.

In this preferred embodiment, the brominating agent is preferably selected from the group consisting of 1,3-dibromo-5,5-dimethylhydantoin and N-bromosuccinimide. More preferably, the brominating agent is 1,3-dibromo-5,5-dimethylhydantoin. In another preferred embodiment, the solvent (S2) is selected from the group consisting of acetonitrile, N,N-dimethylformamide, ethyl acetate, isopropyl acetate, methyl t-butyl ether, tetrahydrofuran, dioxane, dichloromethane, methanol, cyclohexane and hexane. Preferably, the compound of Formula (2) is not isolated during the preparation of Lesinurad (1).

In this embodiment of the first aspect, it is further preferred that the compound of Formula (3) is prepared by a process comprising reaction of a compound of Formula (5):

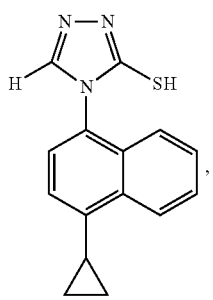

(5)

in the presence of a base (B1) and a solvent (S1), with a compound of Formula (4):

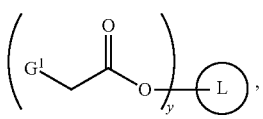

(4)

wherein

L is a linker corresponding with the backbone of a monomeric polyol selected from the group consisting of ethane-1,2-diol and propane-1,2,3-triol;

$G^1$ is a leaving group; and y is 2 or 3.

In this preferred embodiment, the leaving group $G^1$ is preferably a halide, and most preferably, chloride. Preferably, in this preferred embodiment, the solvent (S1) is N,N-dimethylformamide.

In a second aspect of the present invention, there is provided a process for the preparation of a compound of Formula (2):

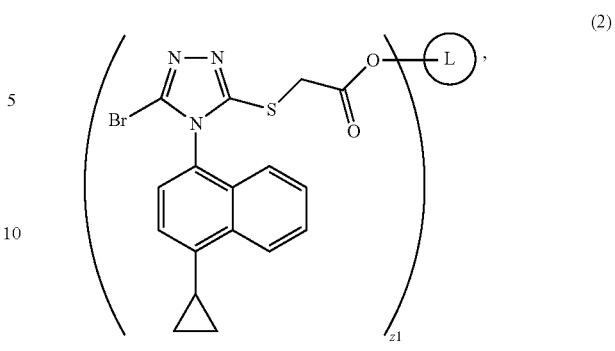

(2)

the process comprising reacting, in the presence of a solvent (S2), a compound of Formula (3):

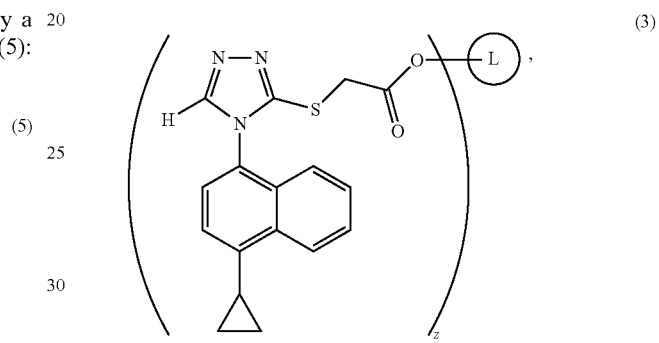

(3)

with a brominating agent, wherein

L is a linker corresponding with the backbone of:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom; and wherein the hydroxyl substituents of the polyol provide the oxygen atoms in the ester connection in the compounds of Formula (2) and Formula (3);

x, z and z1 are each at least 2; and z1≤z≤x.

In a preferred embodiment of the second aspect, the brominating agent is selected from the group consisting of 1,3-dibromo-5,5-dimethylhydantoin and N-bromosuccinimide. Most preferably, the brominating agent is 1,3-dibromo-5,5-dimethylhydantoin.

In a further preferred embodiment of the second aspect, solvent (S2) is selected from the group consisting of acetonitrile, N,N-dimethylformamide, ethyl acetate, isopropyl acetate, methyl t-butyl ether, tetrahydrofuran, dioxane, dichloromethane, methanol, cyclohexane and hexane. Most preferably, solvent (S2) is tetrahydrofuran.

In another preferred embodiment of the second aspect, the compound of Formula (3) is prepared according to the process provided by the third aspect of the present invention, described below. Most preferably, when conducting the process of the invention according to this preferred embodiment, the compound of Formula (3) is not isolated between the processes of the second and third aspects of the invention.

In a third aspect of the present invention, there is provided a process for the preparation of a compound of Formula (3):

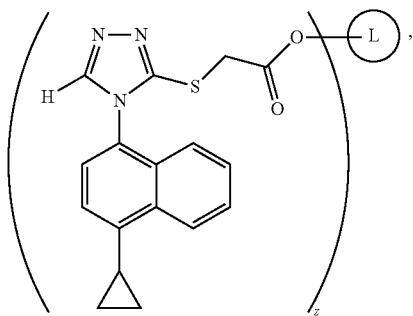

the process comprising reaction of a compound of Formula (5):

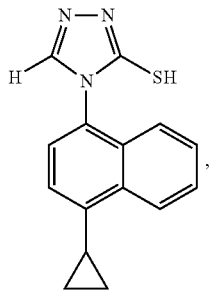

in the presence of a base (B1) and a solvent (S1), with a compound of Formula (4):

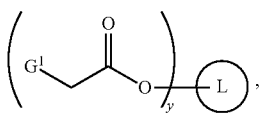

wherein
L is a linker corresponding with the backbone of:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom; and
wherein the hydroxyl substituents of the polyol provide the oxygen atoms in the ester connection in the compounds of Formula (3) and Formula (4);
$G^1$ is a leaving group;
x, y and z are each at least 2; and
$z \leq y \leq x$.

In a preferred embodiment of the third aspect, $G^1$ in the compound of Formula (4) is halide or sulfonate. Most preferably, $G^1$ is halide.

In a further preferred embodiment of the third aspect, base (B1) is a metal bicarbonate. In yet a further preferred embodiment of the third aspect, solvent (S1) is N,N-dimethylformamide.

In further preferred embodiments of the first, second and third aspects of the present invention, L is a linker corresponding with the backbone of a monomeric polyol and x is equal to z1. In these preferred embodiments, x, y and z are equal. In a further preferred embodiment, x is from 2 to 6. In other preferred embodiments, z1 is less than x. In yet further preferred embodiments z is less than y and y is less than x.

In other preferred embodiments of the first, second and third aspects of the present invention, L is a linker corresponding with the backbone of a monomeric polyol selected from the group consisting of C2-C10 aliphatic diols, C3-C10 aliphatic triols, C4-C20 aliphatic tetrols, saccharides and sugar alcohols. In these embodiments, the monomeric polyol is preferably ethane-1,2-diol or propane-1,2,3-triol. Even more preferably, the monomeric polyol is ethane-1,2-diol, and x and Z1 are both 2.

In other preferred embodiments of the first, second and third aspects of the present invention, L is a linker corresponding with the backbone of a polyvinyl alcohol or a polyether alcohol. Preferably, L is a polyvinyl alcohol having a mean molecular weight of from about 30 000 to about 50 000, 87-89% hydrolyzed.

In other preferred embodiments of the first, second and third aspects of the present invention, L is a linker corresponding with the backbone of a water-insoluble polymeric polyol suitable for use as a solid phase support. Preferably, L is selected from the group consisting of hydroxymethyl polystyrene resin, hydroxyethyl polystyrene resin, hydroxybutyl polystyrene resin, 4-(hydroxymethyl)benzoylamidoethyl polystyrene resin, 4-(hydroxymethyl)phenoxymethyl polystyrene resin and hydroxyl functionalized polyethyleneglycol-polystyrene resins.

In a fourth aspect of the present invention, there is provided a compound of Formula (3):

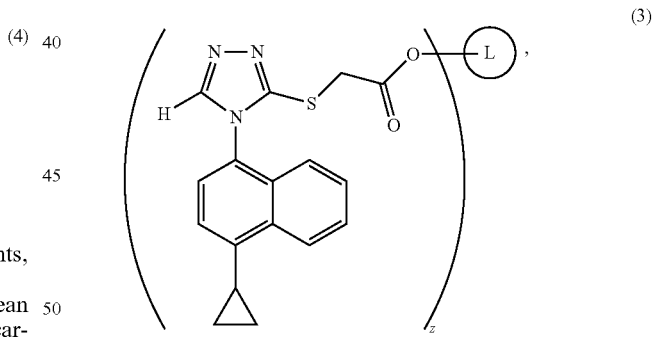

wherein
L is a linker corresponding with the backbone of either:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom; and
wherein the hydroxyl substituents of the polyol provide the oxygen atoms in the ester connection in the compound of Formula (3);
x and z are each at least 2; and
$z \leq x$.

In a preferred embodiment of the fourth aspect, L is a linker corresponding with the backbone of a monomeric polyol and x is equal to z. Preferably, x is from 2 to 6. More preferably, in this preferred embodiment, L is a linker corresponding with the backbone of a monomeric polyol selected from the group consisting of C2-C10 aliphatic diols, C3-C10 aliphatic triols, C4-C20 aliphatic tetrols, saccharides and sugar alcohols. Most preferably, the monomeric polyol is selected from the group consisting of ethane-1,2-diol and propane-1,2,3-triol.

In a further preferred embodiment of the fourth aspect, L is a linker corresponding with the backbone of a polymeric polyol and z is less than x. Preferably, the polymeric polyol is selected from the group consisting of polyvinyl alcohols and polyether alcohols. Most preferably, the polymeric polyol is a polyvinyl alcohol having a mean molecular weight of from about 30 000 to about 50 000, 87-89% hydrolyzed. Alternatively, the polymeric polyol is an insoluble polymer suitable for use as a solid phase support containing x mean hydroxyl groups as substituents to which compounds can be directly or indirectly linked. Preferably, the polymeric polyol is selected from the group consisting of hydroxymethyl polystyrene resin, hydroxyethyl polystyrene resin, hydroxybutyl polystyrene resin, 4-(hydroxymethyl) benzoylamidoethyl polystyrene resin, 4-(hydroxymethyl) phenoxymethyl polystyrene resin and hydroxyl functionalized polyethyleneglycol-polystyrene resins.

In a further preferred embodiment of the fourth aspect the compound of the fifth aspect is selected from:

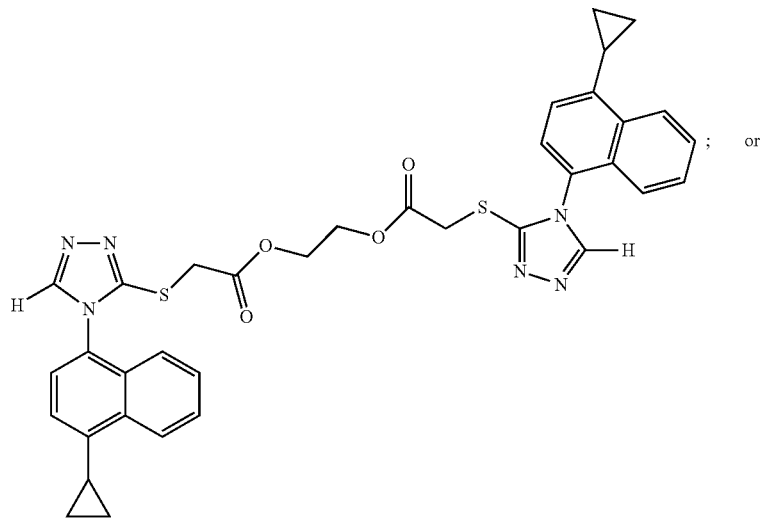

(3-A)

; or

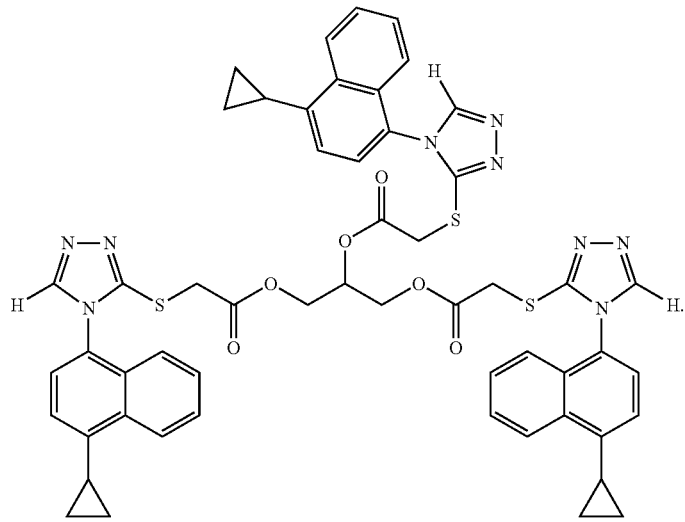

(3-B)

In a fifth aspect of the present invention, there is provided a compound of Formula (2):

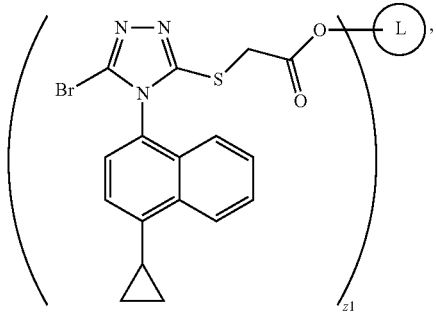

wherein
L is a linker corresponding with the backbone of either:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom; and wherein the hydroxyl substituents of the polyol provide the oxygen atoms in the ester connection in the compound of Formula (2);

x and z1 are each at least 2; and z1≤x.

In a preferred embodiment of the fifth aspect, L is a linker corresponding with the backbone of a monomeric polyol and x is equal to z1. Preferably, x is from 2 to 6. More preferably, in this preferred embodiment, L is a linker corresponding with the backbone of a monomeric polyol selected from the group consisting of C2-C10 aliphatic diols, C3-C10 aliphatic triols, C4-C20 aliphatic tetrols, saccharides and sugar alcohols. Most preferably, the monomeric polyol is ethane-1,2-diol or propane-1,2,3-triol.

In a further preferred embodiment of the fifth aspect, L is a linker corresponding with the backbone of a polymeric polyol and z1 is less than x. Preferably, the polymeric polyol is selected from the group consisting of polyvinyl alcohols and polyether alcohols. Most preferably, the polymeric polyol is a polyvinyl alcohol having a mean molecular weight of from about 30 000 to about 50 000, 87-89% hydrolyzed. Alternatively, the polymeric polyol is an insoluble polymer suitable for use as a solid phase support containing x mean hydroxyl groups as substituents to which compounds can be directly or indirectly linked. Preferably, the polymeric polyol is selected from the group consisting of hydroxymethyl polystyrene resin, hydroxyethyl polystyrene resin, hydroxybutyl polystyrene resin, 4-(hydroxymethyl) benzoylamidoethyl polystyrene resin, 4-(hydroxymethyl) phenoxymethyl polystyrene resin and hydroxyl functionalized polyethyleneglycol-polystyrene resins.

In a further preferred embodiment of the fifth aspect the compound of the fifth aspect is selected from:

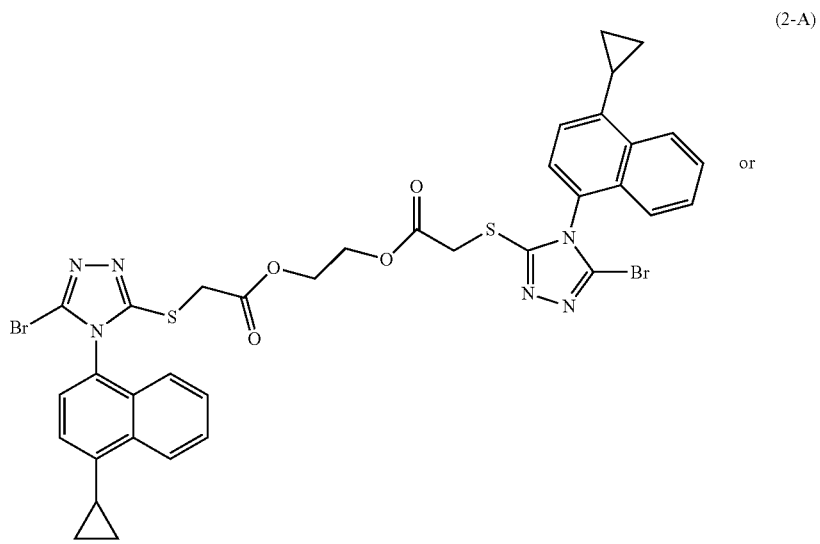

-continued (2-B)

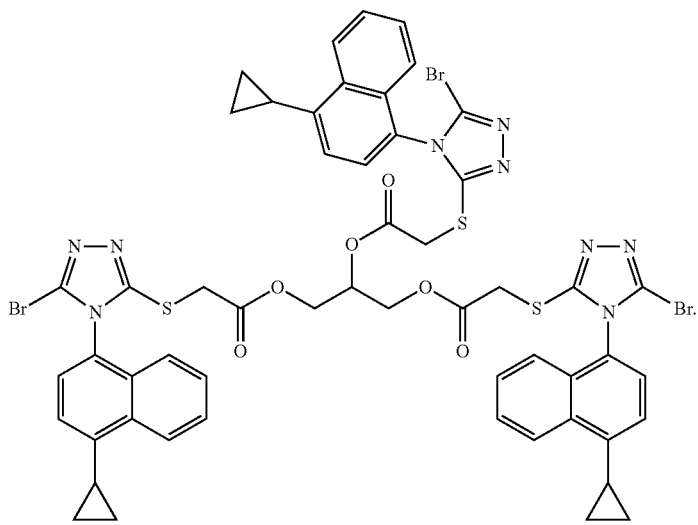

In a sixth aspect of the present invention, there is provided a process for the preparation of Lesinurad (1):

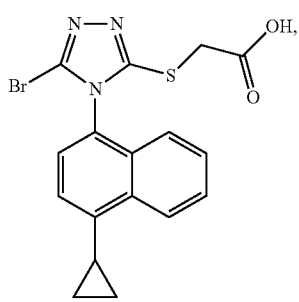
(1)

or a salt thereof, the process comprising:

(i) reaction of a compound of Formula (9):

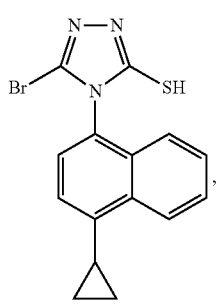
(9)

in the presence of a base (B5) and a solvent (S7), with a compound of Formula (8):

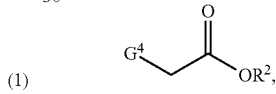
(8)

wherein $R^2$ is selected from the group consisting of H, an aliphatic group, a substituted aliphatic group, aryl, substituted aryl, arylalkyl, substituted arylalkyl; and $G^4$ is a leaving group; and (ii) when $R^2$ is not H, hydrolysis of the product formed in the reaction of the compounds of Formula (8) and Formula (9) to provide Lesinurad (1).

In a preferred embodiment of the sixth aspect, $G^4$ in the compound of Formula (8) is halide or sulfonate. Most preferably, $G^4$ is halide.

In a further preferred embodiment of the sixth aspect, base (B5) is an alkali metal bicarbonate.

In another preferred embodiment of the sixth aspect, solvent (S7) is selected from the group consisting of N-methyl-2-pyrolidone, N,N-dimethylacetamide, N,N-dimethylformamide, dimethyl sulfoxide, acetonitrile, tetrahydrofuran, toluene, dioxane, acetone, methyl isobutyl ketone, methyl t-butyl ether, dichloromethane and water. Most preferably, solvent (S7) is water.

In a further preferred embodiment of the sixth aspect, the hydrolysis of $R^2$ in step (ii) is conducted in the presence of a base (B6), which is an alkali metal hydroxide base, and a solvent (S8), which is selected from the group consisting of water and ethers.

In another preferred embodiment of the sixth aspect, wherein the compound of Formula (9) is prepared by reaction, in the presence of a solvent (S6), of a compound of Formula (10):

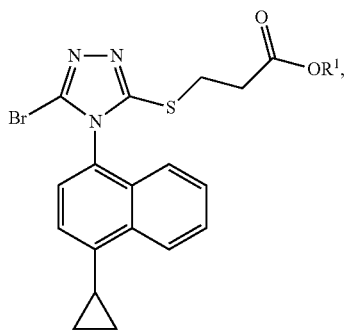

(10)

with a base (B4),
wherein
R is selected from the group consisting of aliphatic, substituted aliphatic, aryl, substituted aryl, arylalkyl and substituted arylalkyl groups.

In this preferred embodiment, base (B4) is preferably a metal hydroxide, and most preferably lithium hydroxide.

In this preferred embodiment, the compound of Formula (10) is prepared by treatment, in the presence of a solvent (S5), of a compound of Formula (11):

(11)

with a brominating agent,
wherein
R¹ is selected from the group consisting of aliphatic, substituted aliphatic, aryl, substituted aryl, arylalkyl and substituted arylalkyl groups.

Preferably, in the bromination of the compound of Formula (11), the brominating agent is selected from the group consisting of 1,3-dibromo-5,5-dimethylhydantoin and N-bromosuccinimide. Most preferably, the brominating agent is N-bromosuccinimide. Preferably, for the bromination of the compound of Formula (11), solvent (S5) is tetrahydrofuran.

In this preferred embodiment, the compound of Formula (11) is prepared by reaction of a compound of Formula (5):

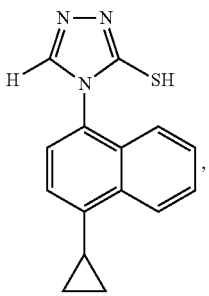

(5)

in the presence of a solvent (S4), with a compound of Formula (12)

(12)

$G^3$ ... $OR^1$, wherein
R¹ is selected from the group consisting of aliphatic, substituted aliphatic, aryl, substituted aryl, arylalkyl and substituted arylalkyl groups; and
G³ is a leaving group.

Preferably, in the compound of Formula (12), G³ is a halide or sulfonate. Most preferably, G³ is a halide.

In the reaction of the compound of Formula (5) with the compound of Formula (12), solvent (S4) is preferably selected from the group consisting of N-methyl-2-pyrolidone, N,N-dimethylacetamide, N,N-dimethylformamide, dimethyl sulfoxide, acetonitrile, tetrahydrofuran, dioxane, dichloromethane and water. Most preferably, solvent (S4) is N,N-dimethylformamide.

In the reaction of the compound of Formula (5) with the compound of Formula (12), it is preferred that the reaction is conducted in the presence of base (B3). Preferably, base (B3) is a metal carbonate. Most preferably, base (B3) is sodium bicarbonate.

Preferably, in this preferred embodiment of the sixth aspect, in the reaction of the compound of Formula (5) with the compound of Formula (12), R¹ in the compound of Formula (12) is C1-C6 alkyl, and R² in the compound of Formula (8) is H. More preferably, R¹ is methyl and R² is H.

In a seventh aspect of the present invention, there is provided a compound of Formula (11):

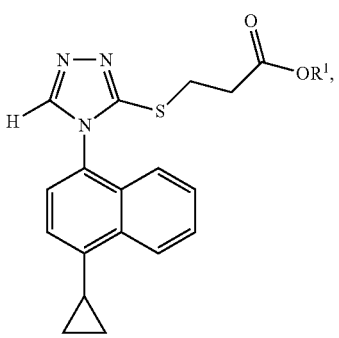

(11)

wherein
R¹ is selected from the group consisting of aliphatic, substituted aliphatic, aryl, substituted aryl, arylalkyl and substituted arylalkyl groups.

In a preferred embodiment of the seventh aspect, R¹ in the compound of Formula (11) is C1-C6 alkyl. Most preferably, R¹ is methyl.

In an eighth aspect of the present invention, there is provided a compound of Formula (10):

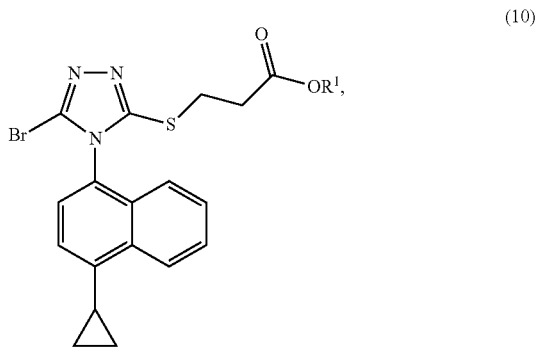

(10)

wherein
R¹ is selected from the group consisting of aliphatic, substituted aliphatic, aryl, substituted aryl, arylalkyl and substituted arylalkyl groups;
with the proviso that R is not ethyl.

In a preferred embodiment of the eighth aspect, R¹ in the compound of Formula (10) is C1 or C3-C6 alkyl. Most preferably, R¹ is methyl.

DETAILED DESCRIPTION

Development of the processes of the present invention followed from the discovery by the inventors that problems associated with the known processes for the preparation of Lesinurad could be addressed through the use of novel protecting group strategies. Based on these discoveries, the present invention provides new processes for the preparation of Lesinurad, as well as new intermediates and processes for the preparation thereof, that are useful in the preparation of Lesinurad. Through the use of these new processes and intermediates, the use of toxic, malodorous and/or corrosive reagents is reduced or eliminated compared to the known processes for the preparation of Lesinurad. Thus, the present invention provides processes for the preparation of Lesinurad that are more amendable to commercial use. Additionally, through the processes of the present invention, it is possible to use the compound of Formula (5) as the starting material, which is accessible in fewer steps compared to the corresponding compound of Formula (A).

As an example, through the use of the soluble polyol linkers in certain embodiments of the present invention, the processes of the invention provide simplified work-up and purification procedures where the water-soluble polyol linkers are easily removed during biphasic extractions.

Furthermore, in embodiments of the present invention, processes are provided which are amenable to solid phase synthetic approaches. In addition to enabling the recovery and recycling of solid phase supports, such processes also allow for simplification of the manufacturing process with respect to the handling of materials and work-up of individual steps.

In other embodiments of the present invention, it has been found that, through the use of the novel protecting group strategies employed, it is possible to lessen the formation of impurities during the bromination step of the process to prepare Lesinurad, which in turn provides a more efficient overall manufacturing process.

As used herein, the designation "C1-Cx" refers to the total number of carbon atoms in the indicated group, including substituent groups, with C1-Cx including C1-02, C1-03 . . . C1-Cx. For example, a group designated as "C1-04" indicates that there are one to four carbon atoms in the moiety, i.e., groups containing 1 carbon atom, 2 carbon atoms, 3 carbon atoms or 4 carbon atoms. Thus, by way of example only, "C1-C4 alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

As used herein, the term "aliphatic", alone or as part of another substituent, means, unless otherwise stated, a straight chain, branched chain or cyclic hydrocarbon radical, or a combination thereof, which may be fully saturated, or mono- or polyunsaturated, and can include di- and multivalent radicals, having the number of carbon atoms designated. Examples of saturated hydrocarbon radicals include, but are not limited to, groups such as methyl, ethyl, n-propyl, iso-propyl, n-butyl, t-butyl, iso-butyl, sec-butyl, hexanyl, 2-methyl-2-hexanyl, cyclohexyl, 1-methylcyclohexyl, cyclopropylmethyl, and isomers of, for example, n-pentyl, n-hexyl, n-heptyl, n-octyl, and the like. An unsaturated hydrocarbon radical is one having one or more double bonds or triple bonds. Examples of unsaturated hydrocarbon radicals include, but are not limited to, vinyl, 2-propenyl, crotyl, 2-isopentenyl, 2-(butadienyl), 2,4-pentadienyl, 3-(1,4-pentadienyl), ethynyl, 1-propynyl, 2-propynyl, 3-butynyl, and the higher homologs and isomers.

As used herein, the term "alkyl", alone or as part of another substituent, means, unless otherwise stated, a straight or branched chain, saturated hydrocarbon radical having the number of carbon atoms designated (e.g., C1-04 means one to four carbon atoms). When there is no indication of the number of carbon atoms in the alkyl, it is meant, unless otherwise indicated by context, that there are from 1 to 10 carbons. Examples of saturated hydrocarbon groups include methyl, ethyl, n-propyl, iso-propyl, n-butyl, t-butyl, iso-butyl and sec-butyl.

As used herein, the term "aryl", alone or as part of another substituent, means, unless otherwise stated, a polyunsaturated, aromatic, hydrocarbon radical which can be a single ring or multiple rings (preferably from 1 to 3 rings) which are fused together or linked covalently having the number of carbon atoms designated. When there is no indication of the number of carbon atoms in the aryl, it is meant, unless otherwise indicated by context, that there are from 6 to 18 carbons. Non-limiting examples of aryl groups include: phenyl, 1-naphthyl, 2-naphthyl and 4-biphenyl.

As used herein, the term "arylalkyl", alone or as part of another substituent, means, unless otherwise stated, an aryl substituent as defined herein attached through an alkyl radical to the parent structure. When there is no indication of the number of carbon atoms in the arylalkyl group, it is meant, unless otherwise indicated by context, that there are from 7 to 20 carbons. Non-limiting examples of arylalkyl groups include benzyl, and phenethyl.

As used herein, the term "substituted" refers to the replacement of one or more hydrogen atoms with any one of a variety of substituents. A substituent may be a non-hydrogen atom or multiple atoms of which at least one is a non-hydrogen atom and one or more may or may not be hydrogen atoms. A substituted group (e.g., substituted —CH$_2$CH$_3$) may be fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). Substituted compounds may comprise substituents selected from the group consisting of: R''', OR'', NR''R''', SR'', halogen, SiR'''R''R''', OCOR''', COR'', CO$_2$R'', CONR''R''', NR''CO$_2$R''', NR''COR''', SOR''', SO$_2$R''', CN, NO$_2$ and CF$_3$. As used herein, each R'' may be selected, independently, from the group consisting of hydrogen, an aliphatic group, aryl and arylalkyl. As used herein, each R' may be selected, independently, from the group consisting of an aliphatic group, aryl and arylalkyl. Examples of substituent groups on substituted aliphatic groups include methoxy, chloro, morpholino, trialkylsilyl such as trimethylsilyl. Examples of substituent groups on substituted aryls include methoxy, methyl, nitro, and chloro.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the context of the present invention, the term "polyol" refers to a compound having two or more hydroxyl groups that can be used as linking sites in the processes of the present invention. Polymers may have a molecular weight ranging from about 1,000 to 200,000.

As used herein, the terms "wt %" or "% w/w" refer to weight percent and is used to express weight solute/weight solution as a percentage.

As used herein, the term "volumes" refers to the parts of solvent or liquids by volume (mL) with respect to the weight of solute (g). For example, when a reaction is conducted using 1 g of starting material and 100 mL of solvent, it is said that 100 volumes of solvent are used.

As used herein, "room temperature" generally refers to a temperature of 20-25° C.

As used herein, the term "about" means "close to" and that variation from the exact value that follows the term is within amounts that a person of skill in the art would understand to be reasonable. For example, when the term "about" is used with respect to temperature, a variation of ±5° C. is generally acceptable when carrying out the processes of the present invention; when used with respect to mole equivalents, a variation of ±0.1 moles is generally acceptable; and when used with respect to volumes, a variation of 10% is generally acceptable.

In one embodiment of the present invention, Lesinurad (1) and intermediates useful in the preparation thereof may be prepared by exemplary processes as set out in Scheme 3. Exemplary reagents and conditions for these reactions are disclosed herein.

In the compounds and processes described herein, L is a linker corresponding with the backbone of either:
  (a) a monomeric polyol having x hydroxyl substituents, each bonded to a different carbon atom;
  (b) a water-soluble polymeric polyol having x mean hydroxyl substituents, each bonded to a different carbon atom; or
  (c) a water-insoluble polymeric polyol suitable for use as a solid phase support having x mean hydroxyl substituents, each bonded to a different carbon atom;
wherein the hydroxyl substituents of the polyol provide the oxygen atoms in the ester connection in the compounds of Formulas (2), (3) and (4);
$G^1$ and $G^2$ are each independently a leaving group;
x, y, z and z1 are each at least 2; and
$z1 \le z \le y \le x$.

In the process of the present invention, L corresponds with the backbone of a polyol bearing two or more hydroxyl substituents which react to form an ester bond with a bifunctional compound of Formula (6), the product of which is further reacted with the compound of Formula (5). In this way, two or more equivalents of the compound of Formula (5) are linked together with the compound of Formula (7), which serves as a protecting group for the carboxylic acid side chain that is added during the linking step before the bromination reaction. Hydrolysis of the ester linkage following bromination liberates Lesinurad (1) and the compound of Formula (7). If desired, in certain embodiments of the invention, the polyol can be recovered following the hydrolysis step and recycled for use in subsequent application of the process.

As illustrated in Scheme 3, x signifies the number of hydroxyl substituents of the polyol. In acknowledgement of the fact that, depending on the polyol used, complete linkage may not occur at all hydroxyl sites on the polyol, or that complete bromination of the triazole ring in the compound of Formula (3) may not occur under all reaction conditions, Scheme 3 refers to x, y, z and z1 as the number of substituents present in the compounds of Formulas (7), (4), (3), and (2), respectively. Ideally, x=y=z=z1. However, in practice, it may be found that x>y>z>z1. Therefore, when practicing the processes of the present invention, assays can, if desired, be carried out to determine or estimate the degree of substitution in any of compounds of Formulas (2), (3), (4) or (7) so that the amount of reactants used can be adjusted accordingly. Preferably, when polyols with more than 3 hydroxyl groups are used, an assay is conducted prior to at the least the bromination of the compound of Formula (3).

In the compounds and processes described herein, the monomeric polyol is selected from the group consisting of diols, triols, tetrols, pentols, sugar alcohols and saccharides, which are discrete compounds having two or more hydroxyl groups. Preferably, the monomeric polyol has from 2 to 8 hydroxyl substituents.

Diols useful as polyols in the processes of the present invention preferably have from 2 to 10 carbon atoms, more preferably from 2 to 4 carbons. Preferably, diols are selected from the group consisting of ethanediol (ethylene glycol), propanediol (propylene glycol), butanediol, pentanediol, and hexanediol, and their isomers and higher homologs, cyclohexanediol, 2-(2-hydroxyethoxy)ethan-1-ol (diethylene glycol) and 4-oxa-2,6-heptanediol (dipropylene glycol), 4,4'-(propane-2,2-diyl)diphenol (BPA) and benzene-1,3-diol (resorcinol). More preferably, diols are selected from the group consisting of ethylene glycol and propylene glycol. Most preferably, the diol is ethylene glycol.

Triols useful as polyols in the processes of the present invention preferably have 3 to 10 carbon atoms. Preferably, triols are selected from the group consisting of propane-1,2,3-triol (glycerol), 2-(hydroxymethyl)-2-ethylpropane-1,3-diol (TMP or trimethylolpropane), 2-(hydroxymethyl)-2- methylpropane-1,3-diol (TME or trimethylolethane), 1,2,4-butanetriol, and their isomers and higher homologs, including 1,2,6-hexanetriol and 1,2,10-decanetriol. More preferably, triols are selected from the group consisting of glycerol, 2-(hydroxymethyl)-2-ethylpropane-1,3-diol, and 2-(hydroxymethyl)-2-methylpropane-1,3-diol. Most preferably, the triol is glycerol.

Tetrols useful as polyols in the processes of the present invention preferably have from 4 to 20 carbon atoms. Preferably, tetrols are selected from the group consisting of 2,2-bis(hydroxymethyl)propane-1,3-diol (pentaerythritol), butane-1,2,3,4-tetrol (erythritol) and bis(2,3-dihydroxypropyl) ether (diglycerol). Most preferably, the tetrol is erythritol.

Pentols useful as polyols in the processes of the present invention preferably have from 4 to 20 carbon atoms. Preferably, pentols are selected from the group consisting of xylitol, arabitol, ribitol, and 6-methoxycyclohexane-1,2,3,4,5-pentol (pinitol). Most preferably, the pentol is xylitol or pinitol.

Sugar alcohols are preferably selected from the group consisting of inositol, mannitol, maltitol, sorbitol, and xylitol.

Saccharides are refers to mono- or disaccharides, and are preferably selected from the group consisting of glucose, sucrose and lactose.

In the compounds and processes described herein, preferably, the polymeric polyol is either a water-soluble polymeric polyol or a water-insoluble polymeric polyol.

In the context of the present invention, the mean molecular weight of polymeric polyols corresponds with a mean molecular weight cited by a commercial source or, when a molecular weight range is given, to the calculated mean of the range regardless of the distribution of chain lengths. For example, when a commercial source cites a molecular weight range of 31,000 to 50,000, the mean molecular weight is taken to be 40,500. This number is used to calculate mean values of x, y, z and z1.

Water-soluble polymeric polyols are hydroxyl-functionalized polymers, preferably selected from the group consisting of polyvinyl alcohols (PVA) and polyethers (i.e., diols, triols or tetrols). These polymers may have a molecular weight ranging from about 1,000 to 200,000.

The PVA can vary by mean molecular weight and degree of saponification (i.e., hydrolysis). Preferably, the PVA has a mean molecular weight of from about 5,000 to about 200,000, more preferably from about 20,000 to about 100,000, and most preferably from about 30,000 to about 50,000 g/mol. The PVA preferably has a degree of saponification greater than about 80%, more preferably greater than about 97%, and most preferably greater than about 99%.

The polyether is preferably selected from the group consisting of polyether diols, polyether triols and polyether tetrols. Most preferably, the polyether diol is a polyethylene glycol (PEG). Preferably, the PEG has a mean molecular weight of 200 to 200 000. More preferably, the PEG is selected from the group consisting of PEG 200, PEG 300, PEG 400, PEG 600, PEG 1000, PEG 1500, PEG 4000, PEG 6000, and PEG 8000. Most preferably, the PEG is PEG 200.

Water-insoluble polymers are hydroxyl-containing polymers useful as a support for solid phase chemistry. Preferred water-insoluble polymers are selected from gel-type polymers and modified surface-type polymers.

"Gel-type polymer" refers to a polymer network that is flexible and able to accommodate substrates within the gel. Gel-type polymers are preferably based on polymers selected from the group consisting of lightly cross-linked (1-2% divinyl benzene) polystyrene, polyethyleneglycol-polystyrene (PEG-PS) and polyacrylate.

The polymers based on polystyrene are hydroxyl functionalized polystyrene resins, preferably selected from the group consisting of hydroxymethyl polystyrene resin, hydroxyethyl polystyrene resin, hydroxybutyl polystyrene resin, 4-(hydroxymethyl)benzoylamidoethyl (HMBA) polystyrene resin and 4-(hydroxymethyl)phenoxymethyl polystyrene resin (Wang resin).

The polymers based on PEG-PS are preferably selected from the group consisting of TENTAGEL® diol, 4-(hydroxymethyl)phenoxyethyl TENTAGEL® resin (Wang-type resin) and ARGOGEL™-OH resin.

The polymers based on polyacrylate are preferably selected from the group consisting of poly (2-hydroxyethyl acrylate) (pHEA), poly (2-hydroxyethyl methacrylate) (pHEMA) and poly(l-glycerol methacrylate). Preferably, the polyacrylate has a mean molecular weight of 20,000 to 300,000. Most preferably, the polyacrylate is pHEMA.

"Modified surface-type polymer" refers to a combination of a mobile polymer grafted to a rigid and inert polymer. The modified surface-type polymers are based on flexible polymers, preferably selected from any of the gel type resins described herein, grafted onto rigid polymers, preferably selected from the group consisting of celluloses and polyolefins. The rigid polymers are preferably in the form of membranes or impermeable particles such as beads, pellets and disks.

In one embodiment of the present invention, there is provided a process for the preparation of a compound of Formula (4):

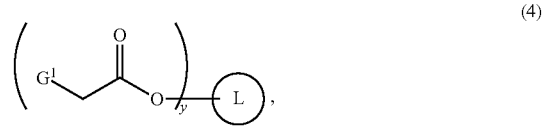

the process comprising reaction of a compound of Formula (7):

with a compound of Formula (6):

wherein
L is a linker corresponding with the backbone of either:
  (a) a monomeric polyol having x hydroxyl substituents, each bonded to a different carbon atom;
  (b) a water-soluble polymeric polyol having x mean hydroxyl substituents, each bonded to a different carbon atom; or
  (c) a water-insoluble polymeric polyol suitable for use as a solid phase support having x mean hydroxyl, each bonded to a different carbon atom;

wherein the hydroxyl substituents of the polyol provide the oxygen atoms in the ester connection in the compounds of Formulas (2), (3) and (4);

$G^1$ and $G^2$ are each independently a leaving group;

x and y are each at least 2; and y≤x.

In the compound of Formula (6), $G^1$ is a leaving group selected from the group consisting of halide and a sulfonate, such as methane sulfonate or toluene sulfonate. Preferably, $G^1$ is halide, and more preferably, is chloride. In the compound of Formula (6), $G^1$ and $G^2$ may be the same or different. $G^2$ is a leaving group selected from the group consisting of halide and OR, wherein R is selected from the group consisting of acyl, aliphatic, arylalkyl and succinimidyl. Preferably, $G^2$ is a halide, and more preferably, chloride. If $G^1$ and $G^2$ are the same, preferably, $G^1$ and $G^2$ are both halide.

In the reaction of a compound of Formula (6) and a compound of Formula (7), preferably an amount of x molar equivalents of the compound of Formula (6) is used. However, if desired, an excess of from about 1.1 to about 10 molar equivalents of the compound of Formula (6) may be used with respect to x, the number of hydroxyl groups present. Preferably, the excess used is between about 1.1 and about 2.0 molar equivalents.

In the reaction of a compound of Formula (6) and a compound of Formula (7), any generated acid by-product is preferably neutralized by a base (B0), which may be any suitable inorganic or organic base. Base (B0) is preferably selected from the group consisting of tertiary amines, metal carbonates, metal bicarbonates and metal hydroxides. Preferably, base (B0) is selected from the group consisting of sodium hydroxide, potassium hydroxide, lithium hydroxide, sodium carbonate, sodium bicarbonate, potassium carbonate, potassium bicarbonate, lithium carbonate, potassium phosphate, sodium phosphate, triethylamine, diisopropylethylamine, N,N-dimethylaniline, N,N-diethylaniline, pyridine, and mixtures thereof. More preferably, base (B0) is selected from metal carbonates and metal bicarbonates. Most preferably, base (B0) is sodium carbonate.

The reaction of a compound of Formula (6) and a compound of Formula (7) may be conducted in the presence of a solvent (S0) or it may be conducted without using solvent (neat). Preferably, the reaction is conducted in the presence of solvent (S0) selected from the group consisting of N-Methyl-2-pyrrolidone, dichloromethane, tetrahydrofuran, ethyl acetate, dioxane, methyl t-butyl ether and acetonitrile. Most preferably, solvent (S0) is N-Methyl-2-pyrrolidone or dichloromethane.

The reaction of a compound of Formula (6) and a compound of Formula (7) is conducted at any suitable temperature. Preferably, the temperature is in the range of about 20° C. to about 60° C., more preferably between about 30° C. and about 50° C.

In another embodiment of the present invention, there is provided a process for the preparation of a compound of Formula (3):

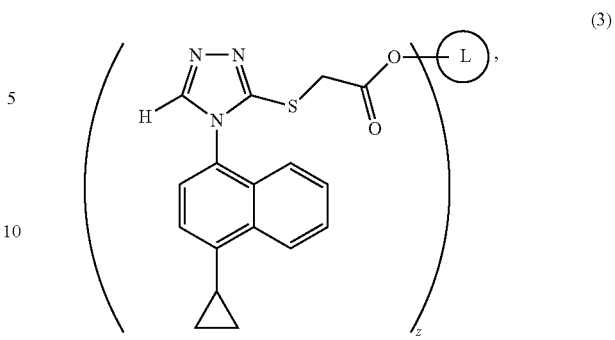

the process comprising reaction of a compound of Formula (5):

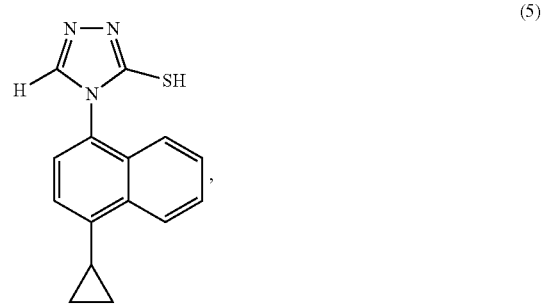 [SMILES: Sc1nncn1-c1ccc(C2CC2)c2ccccc12]

in the presence of a base (B1) and a solvent (S1), with a compound of Formula (4)

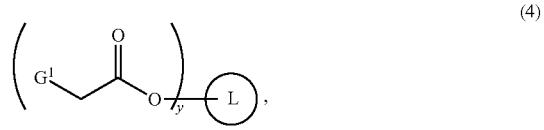

wherein

L is as described above $G^1$ is a leaving group;

x, y and z are each at least 2; and z≤y≤x.

In the compound of Formula (4), $G^1$ is a leaving group. The leaving group $G^1$ is preferably selected from the group consisting of halide and a sulfonate, such as methane sulfonate or toluene sulfonate. Most preferably, $G^1$ is halide.

In the reaction of a compound of Formula (4) and a compound of Formula (5), it is preferred, especially when L corresponds with the backbone of a polymeric polyol, that an assay is conducted to determine the degree of substitution, y, in order to determine the amount of the compound of Formula (5) to be used, as well as to monitor the yield of the reaction.

The reaction of a compound of Formula (4) and a compound of Formula (5) is conducted in the presence of a base (B1). Base (B1) may be any suitable inorganic or organic base, and is preferably selected from the group consisting of tertiary amines, metal carbonates, metal bicarbonates and metal hydroxides. Base (B1) is preferably selected from the group consisting of sodium hydroxide, potassium hydroxide, lithium hydroxide, sodium carbonate, sodium bicarbonate, potassium carbonate, potassium bicarbonate, lithium carbonate, potassium phosphate, sodium phosphate, triethylamine, diisopropylethylamine, N,N-dimethylaniline, N,N-diethylaniline, pyridine, and mixtures thereof. More preferably, base (B1) is selected from the group consisting of metal carbonates and metal bicarbonates. Most preferably, base (B1) is sodium bicarbonate.

The reaction of a compound of Formula (4) and a compound of Formula (5) is conducted in the presence of a solvent (S1). Preferably, the solvent (S1) is selected from the group consisting of N-methyl-2-pyrolidone (NMP), N,N-dimethylacetamide (DMA), N,N-dimethylformamide, dimethyl sulfoxide (DMSO), acetonitrile, tetrahydrofuran, toluene, dioxane, acetone, methyl isobutyl ketone (MIBK), methyl t-butyl ether and water. Most preferably, solvent (S1) is N,N-dimethylformamide.

The reaction of a compound of Formula (4) and a compound of Formula (5) is conducted at any suitable temperature. Preferably, the temperature is in the range of about 15° C. to about 80° C., more preferably between about 20° C. and about 30° C.

Following the reaction of the compound of Formula (4) and a compound of Formula (5), the compound of Formula (3) may react with a brominating agent to afford the compound of Formula (2), which may be further hydrolysed to Lesinurad (1), as described herein. This sequence may be telescoped, whereby the compounds of Formula (3) and Formula (2) are not isolated prior to isolation of Lesinurad (1). Alternatively, the compounds of Formula (3) and Formula (2) may be isolated.

In another embodiment of the present invention, there is provided a process for the preparation of a compound of Formula (2):

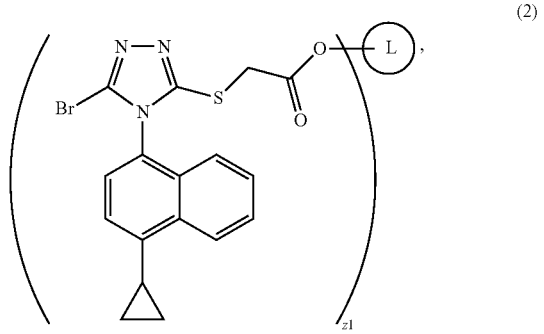

(2)

the process comprising reacting, in the presence of a solvent (S2), a compound of Formula (3):

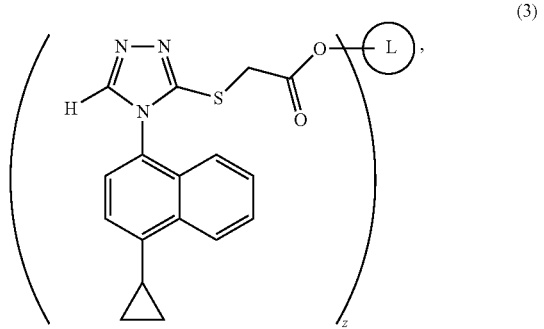

(3)

with a brominating agent,
wherein L is as defined above;
z and z1 are each at least 2; and
z1≤z.

In the bromination reaction, the brominating agent is preferably selected from suitable brominating agents, such as 1,3-dibromo-5,5-dimethylhydantoin (DBDMH), N-bromosuccinimide (NBS), $Br_2$, $BrCl/Br_2$, tetrabutylammoniumtribromide, ammonium bromide/oxone (in methanol and/or water), selenium dibromide, $FeBr_3/Br_2$, $AlCl_3/Br_2$, $FeCl_3/Br_2$, $ZnCl_2/Br_2$, 1,2-dipyridiniumtribromideethane, NBS/acid (trifluoromethanesulfonic acid and $BF_3$—$H_2O$), NBS/concentrated sulfuric acid, NBS/tetrabutylammonium bromide, LiBr/PhI/m-chloroperbenzoic acid/TsOH, $AuCl_3$/NBS, NBS/$Pd(OAc)_2$, N,N,N',N'-etrabromobenzene-1,3-disulfonylamide/poly[N-bromobenzene-1,3-disulfonylamide], $LiTMP/ZnCl_2/Br_2$ and $[Ir(COD)(OMe)]_2/B_2pin_2/$dtbpy/$CuBr_2$. Preferably, so as to avoid the use of reagents comprised of heavy metals, the brominating agent is selected from 1,3-dibromo-5,5-dimethylhydantoin (DBDMH), N-bromosuccinimide (NBS), $Br_2$, $BrCl/Br_2$, tetrabutylammoniumtribromide, ammonium bromide/oxone (in methanol and/or water), 1,2-dipyridiniumtribromideethane, NBS/acid (trifluoromethanesulfonic acid and $BF_3$—$H_2O$), NBS/concentrated sulfuric acid, NBS/tetrabutylammonium bromide, LiBr/PhI/m-chloroperbenzoic acid/TsOH, and N,N,N',N'-tetrabromobenzene-1,3-disulfonylamide/poly[N-bromobenzene-1,3-disulfonylamide]. More preferably, the brominating agent is selected from DBDMH and NBS. Most preferably, the brominating agent is DBDMH.

In the bromination of the compound of Formula (3), preferably an amount of at least z molar equivalents of brominating agent is used. However, if desired, an excess of brominating agent may also be used. Preferably, so as to minimize the formation of impurities, the excess of brominating agent is 1.5 equivalents or less, and more preferably, 1.2 equivalents or less.

Preferably, and in particular when L corresponds with the backbone of a polymeric polyol, the amount of brominating agent required will be determined by assaying the compound of Formula (3) to determine the degree of substitution (z). Preferably, the assay is conducted by $^1H$ NMR, although any suitable method may be used.

The bromination of the compound of Formula (3) is preferably conducted in the absence of light. Alternatively, the reaction may be conducted in the presence of a suitable free radical inhibitor, such as butylated hydroxytoluene (BHT), hydroquinone, tert-butyl hydroquinone, 4-methoxy phenol, benzoquinone, tert-butyl pyrocatechol and phenothiazine. If used, preferably, the inhibitor is BHT.

The bromination of the compound of Formula (3) is conducted in the presence of a solvent (S2). Solvent (S2) is preferably selected from the group consisting of acetonitrile (ACN), N,N-dimethylformamide (DMF), ethyl acetate, isopropyl acetate, methyl t-butyl ether (MTBE), tetrahydrofuran, (2)-methyltetrahydrofuran, dioxane, dichloromethane (DCM), methanol (MeOH), toluene, cyclohexane, and hexane. More preferably, solvent (S2) is selected from the group consisting of tetrahydrofuran, (2)-methyltetrahydrofuran, toluene, dichloromethane and acetonitrile. Most preferably, solvent (S2) is tetrahydrofuran.

The bromination of the compound of Formula (3) may be conducted at any suitable temperature. Preferably, the temperature is in the range of about 20° C. to about 40° C., more preferably between about 25° C. and about 35° C.

Following the reaction of the compound of Formula (3) with the brominating agent, excess brominating agent may be quenched using any suitable quenching agent. Suitable quenching agents include ascorbic acid and sodium thiosulfate.

Following the bromination of the compound of Formula (3) to produce the compound of Formula (2), the compound of Formula (2) may be hydrolysed to Lesinurad (1) as described herein. This sequence may be telescoped, whereby the compound of Formula (2) is not isolated prior to hydrolysis to Lesinurad (1). Alternatively, the compound of Formula (2) may be isolated prior to hydrolysis to Lesinurad (1).

In another embodiment of the present invention, there is provided a process for the preparation of Lesinurad (1):

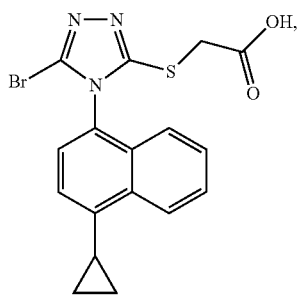
(1)

or a salt thereof, the process comprising hydrolysis, in the presence of a solvent (S3), of a compound of Formula (2):

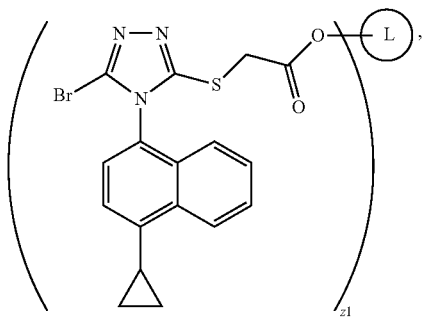
(2)

wherein L and z1 are as defined above.

Hydrolysis of the compound of Formula (2) is preferably conducted in the presence of a suitable acid or a base (B2). Suitable acids include aqueous solutions of trifluoroacetic acid, aqueous solutions of mineral acids such as hydrogen chloride, hydrogen bromide and sulfuric acid and aqueous solutions of sulfonic acids such as methane sulfonic acid and toluene sulfonic acid.

Suitable bases (B2) include, for example, tertiary amines, metal carbonates, metal bicarbonates and metal hydroxides. The base (B2) is preferably selected from the group consisting of sodium hydroxide, potassium hydroxide, lithium hydroxide, sodium carbonate, sodium bicarbonate, potassium carbonate, potassium bicarbonate, lithium carbonate, potassium phosphate, sodium phosphate, triethylamine, diisopropylethylamine, N,N-dimethylaniline, N,N-diethylaniline, pyridine, and mixtures thereof. More preferably, the base (B2) is an alkali metal hydroxide selected from lithium hydroxide, sodium hydroxide and potassium hydroxide. Most preferably, base (B2) is lithium hydroxide.

Hydrolysis of the compound of Formula (2) is conducted in the presence of a solvent (S3). While any suitable solvent may be used, solvent (S1) is preferably selected from the group consisting of water and ethers such as dioxane and tetrahydrofuran (THF). Most preferably solvent (S3) is tetrahydrofuran.

The hydrolysis of the compound of Formula (2) may be conducted at any suitable temperature. Preferably, the temperature is in the range of about 0° C. to about 30° C., more preferably between about 0° C. and about 25° C.

In another embodiment of the present invention, there is provided a compound of Formula (3):

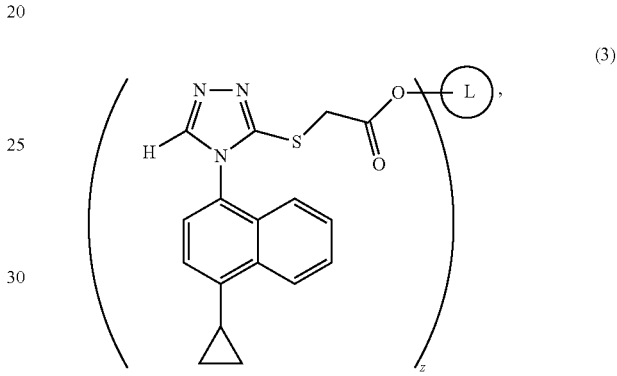
(3)

wherein L and z are as defined above.

In another embodiment of the present invention, there is provided a compound of Formula (2):

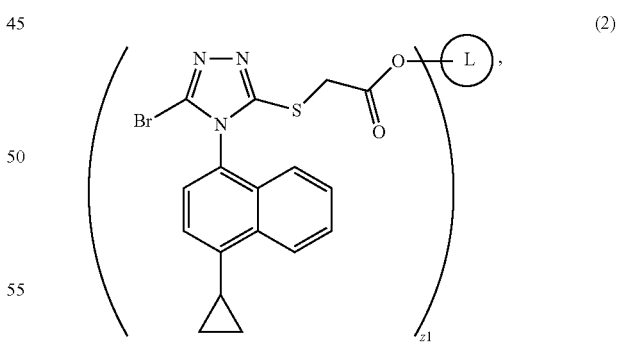
(2)

wherein
L and z1 are as defined above.

In preferred embodiments of the present invention, Lesinurad (1) is prepared by the following exemplary processes utilizing either the monomeric polyol ethylene glycol (Compound of Formula (7-A)) as illustrated in Scheme 5 or using the polymeric polyol polyvinyl alcohol (Compound of Formula (7-C)) as illustrated in Scheme 6.

Scheme 5
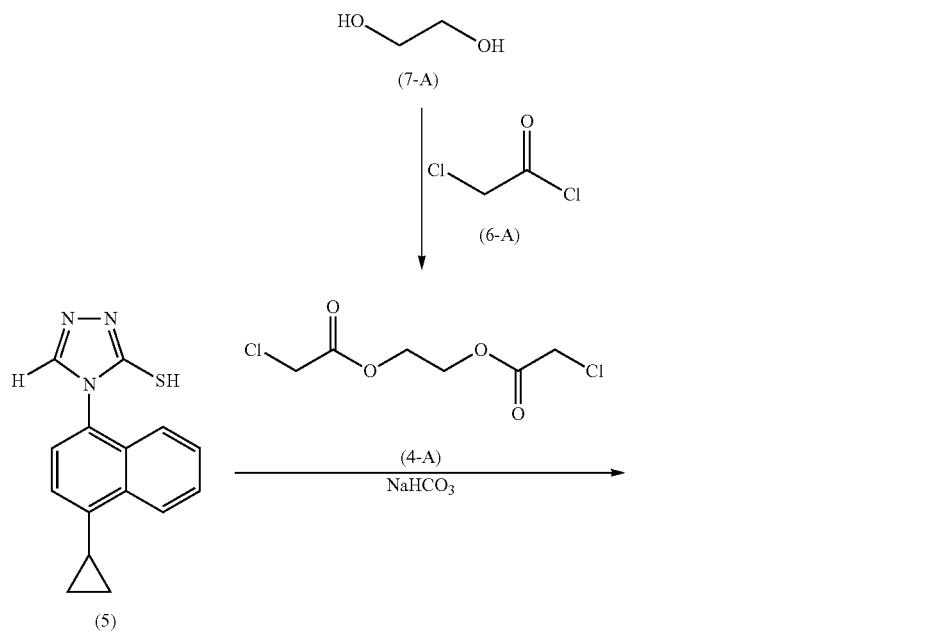
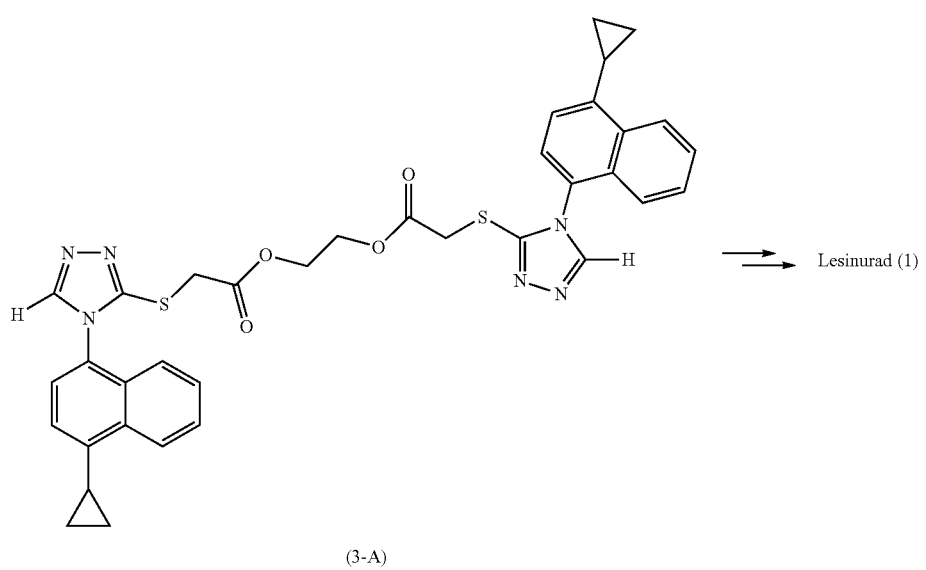
(3-A) → Lesinurad (1)

Scheme 6

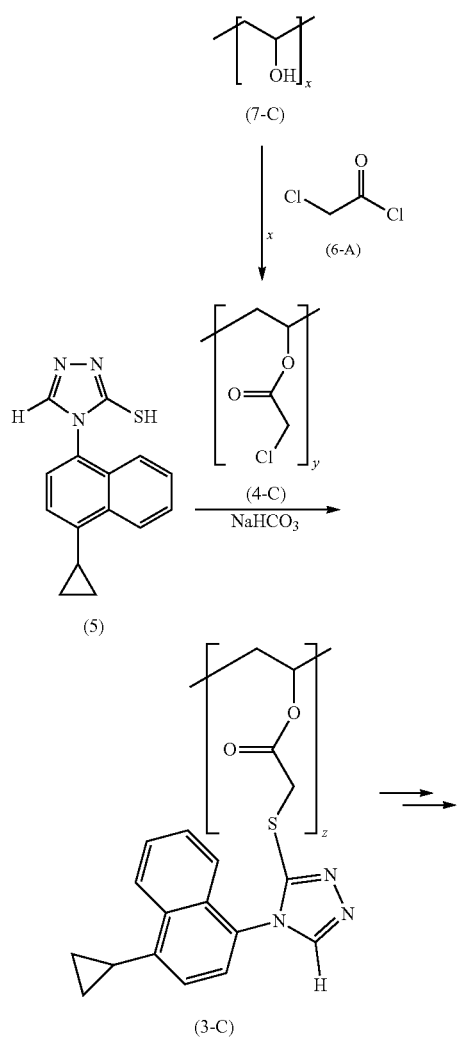

In other embodiments of the present invention, Lesinurad (1) and the intermediates thereof are prepared by exemplary processes as set out in Scheme 4. Exemplary reagents and conditions for these reactions are disclosed herein.

In the compounds and processes of the embodiments set out in Scheme 4, $R^1$ is selected from the group consisting of an aliphatic group, a substituted aliphatic group, aryl, substituted aryl, arylalkyl and substituted arylalkyl; and $R^2$ is H or $R^1$. The aliphatic group is preferably selected from the group consisting of methyl, ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, isomers of n-pentyl, isomers of n-hexyl, isomers of n-heptyl, and isomers of n-octyl. More preferably, the aliphatic group is C1-C6 alkyl, and most preferably methyl. Substituted aliphatic group are preferably substituted with methoxy, trialkylsilyl or halide. The aryl group is preferably selected from the group consisting of phenyl, 1-naphthyl, 2-naphthyl and 4-biphenyl, most preferably phenyl. The substituted aryl group is preferably substituted with one or more substituents selected from the group consisting of R''', OR''', halogen, and $NO_2$, wherein each R''' is methyl. The arylalkyl group is preferably selected from the group consisting of benzyl and phenethyl. Substituted arylalkyl groups are preferably substituted with one or more substituents selected from the group consisting of R''', OR''', halogen and $NO_2$, wherein each R''' is methyl.

In another embodiment of the present invention, there is provided a process for the preparation of a compound of Formula (11):

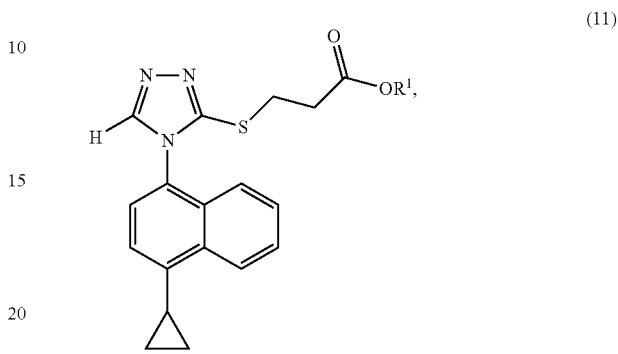

the process comprising reaction of a compound of Formula (5):

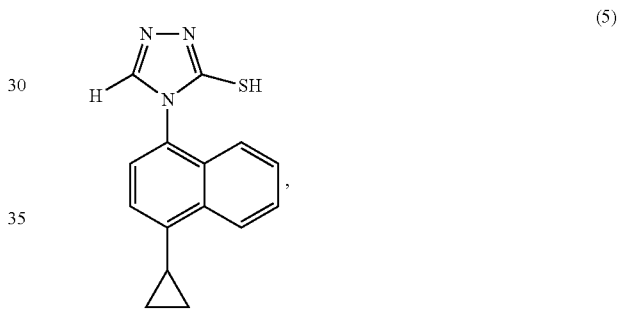

in the presence of a solvent (S4), with a compound of Formula (12)

wherein $R^1$ is as defined above.

In the compound of Formula (12), $G^3$ is a leaving group. The leaving group $G^3$ may be selected from the group consisting of halide and a sulfonate such as methane sulfonic acid or toluene sulfonic acid. Preferably, $G^3$ is bromide.

The reaction of a compound of Formula (5) and a compound of Formula (12) is optionally conducted in the presence of a base (B3). Base ($B_3$) may be any suitable inorganic or organic base, and is preferably selected from the group consisting of tertiary amines, metal carbonates, metal bicarbonates and metal hydroxides. Preferably, base (B3) is selected from the group consisting of sodium hydroxide, potassium hydroxide, lithium hydroxide, sodium carbonate, sodium bicarbonate, potassium carbonate, potassium bicarbonate, lithium carbonate, potassium phosphate, sodium phosphate, triethylamine, diisopropylethylamine, N,N-dimethylaniline, N,N-diethylaniline, pyridine, and mixtures thereof. Most preferably, base (B3) is sodium carbonate.

The reaction of a compound of Formula (5) and a compound of Formula (12) is conducted in the presence of a solvent (S4). Preferably, the solvent (S4) is selected from the group consisting of N-methyl-2-pyrolidone, N,N-dimethylacetamide, N,N-dimethylformamide, dimethyl sulfoxide, acetonitrile, tetrahydrofuran, dioxane, dichloromethane and water. Most preferably, solvent (S4) is R', N-dimethylformarnide.

The reaction of a compound of Formula (5) and a compound of Formula (12) is conducted at any suitable temperature. Preferably, the temperature is in the range of about 40° C. to about 80° C., more preferably between about 50° C. and about 70° C.

In another embodiment of the present invention, there is provided a process for the preparation of a compound of Formula (10):

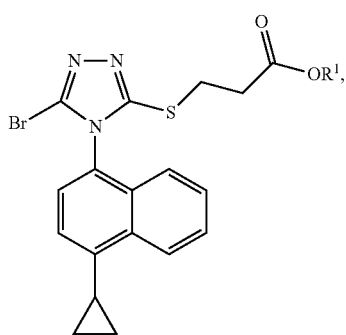

(10)

the process comprising treatment, in the presence of a solvent (S5), of a compound of Formula (11):

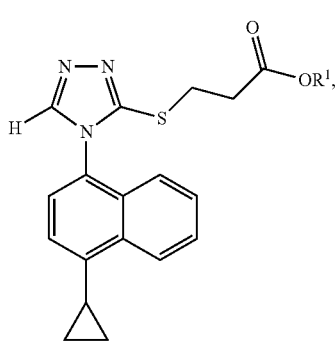

(11)

with a brominating agent,
wherein R¹ is as defined above.

In the bromination reaction of the compound of Formula (11), the brominating agent is preferably selected from suitable brominating agents, such as 1,3-dibromo-5,5-dimethylhydantoin (DBDMH), N-bromosuccinimide (NBS), Br₂, BrCl/Br₂, tetrabutylammoniumtribromide, ammonium bromide/oxone (in methanol and/or water), selenium dibromide, FeBr₃/Br₂, AlCl₃/Br₂, FeCl₃/Br₂, ZnCl₂/Br₂, 1,2-dipyridiniumtribromideethane, NBS/acid (trifluoromethanesulfonic acid and BF₃—H₂O), NBS/concentrated sulfuric acid, NBS/tetrabutylammonium bromide, LiBr/PhI/m-chloroperbenzoic acid/TsOH, AuCl₃/NBS, NBS/Pd(OAc)₂, N,N,N',N'-tetrabromobenzene-1,3-disulfonylamide/poly[N-bromobenzene-1,3-disulfonylamide], LiTMP/ZnCl₂/Br₂ and [Ir(COD)(OMe)]2/B₂pin₂/dtbpy/CuBr₂. Preferably, so as to avoid the use of reagents comprised of heavy metals, the brominating agent is selected from DBDMH, NBS, Br₂, BrCl/Br₂, tetrabutylammoniumtribromide, ammonium bromide/oxone (in methanol and/or water), 1,2-dipyridiniumtribromideethane, NBS/acid (trifluoromethanesulfonic acid and BF₃—H₂O), NBS/concentrated sulfuric acid, NBS/tetrabutylammonium bromide, LiBr/PhI/m-chloroperbenzoic acid/TsOH, and N, N, N',N'-tetrabromobenzene-1,3-disulfonylamide/poly[N-bromobenzene-1,3-disulfonylamide].

More preferably, the brominating agent is selected from DBDMH and NBS. Most preferably, the brominating agent is NBS.

The bromination of the compound of Formula (11) is preferably conducted in the absence of light. Alternatively, the reaction may be conducted in the presence of a suitable free radical inhibitor, such as butylated hydroxytoluene (BHT), hydroquinone, tert-butyl hydroquinone, 4-methoxy phenol, benzoquinone, tert-butyl pyrocatechol and phenothiazine. If used, preferably, the inhibitor is BHT.

The bromination of the compound of Formula (11) is conducted in the presence of a solvent (S5). Solvent (S5) is preferably selected from the group consisting of acetonitrile, N,N-dimethylformamide, ethyl acetate, isopropyl acetate, methyl t-butyl ether, tetrahydrofuran, dioxane, dichloromethane, methanol, cyclohexane and hexane. Most preferably, solvent (S5) is tetrahydrofuran.

The bromination of the compound of Formula (11) may be conducted at any suitable temperature. Preferably, the temperature is in the range of about 20° C. to about 40° C., more preferably between about 25° C. and about 35° C.

Following the reaction of the compound of Formula (11) with the brominating agent, excess brominating agent may be quenched using any suitable quenching agent. Suitable quenching agents include ascorbic acid and sodium thiosulfate.

In another embodiment of the present invention, there is provided a process for the preparation of a compound of Formula (9):

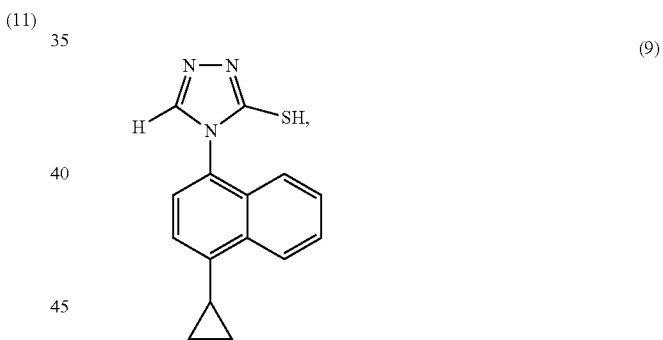

(9)

the process comprising reaction, in the presence of a solvent (S6), of a compound of Formula (10):

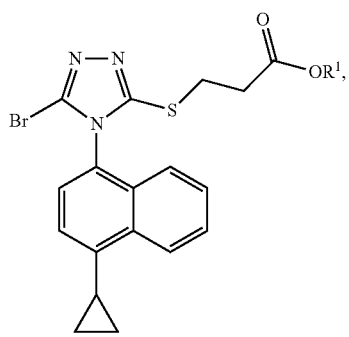

(10)

with a base (B4),
wherein R¹ is as defined above.

Base (B₄) can be any suitable base, but is preferably a metal hydroxide. Most preferably, base (B4) is lithium hydroxide.

The reaction of a compound of Formula (10) and base (B4) is conducted in the presence of a solvent (S6). Preferably, the solvent (S6) is selected from the group consisting of water and ethers such as dioxane and tetrahydrofuran. Most preferably, solvent (S6) is tetrahydrofuran.

The reaction of a compound of Formula (10) and base (B4) is conducted at any suitable temperature. Preferably, the temperature is in the range of about 15° C. to about 30° C., more preferably between about 20° C. and about 25° C.

In another embodiment of the present invention, there is provided a process for the preparation of Lesinurad (1):

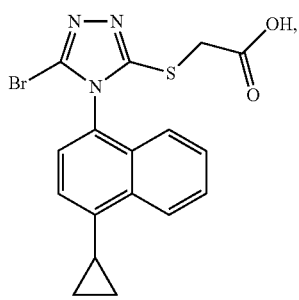

(1)

or a salt thereof, the process comprising:
(i) reaction of a compound of Formula (9):

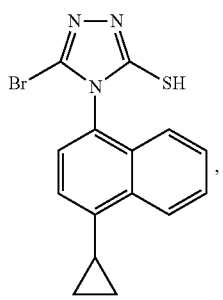

(9)

in the presence of a base (B5) and a solvent (S7), with a compound of Formula (8):

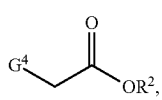

(8)

wherein $G^4$ is a leaving group, and
$R^2$ is as defined above; and
(ii) if required when $R^2$ is not H, hydrolysis of the compound of formula (13):

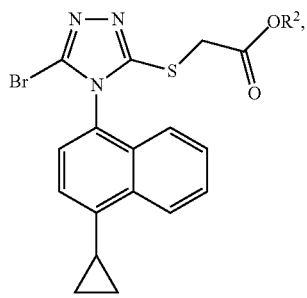

(13)

to form Lesinurad (1).

In the compound of Formula (8), $G^4$ is a leaving group. The leaving group $G^4$ is preferably selected from the group consisting of halide and a sulfonate, such as methane sulfonic acid or toluene sulfonic acid. Preferably, $G^4$ is bromide.

The reaction of a compound of Formula (8) and a compound of Formula (9) is conducted in the presence of a base (B5). Base (B₅) may be any suitable inorganic or organic base, and is preferably selected from the group consisting of tertiary amines, metal carbonates, metal bicarbonates and metal hydroxides. Preferably, base (B5) is selected from the group consisting of sodium hydroxide, potassium hydroxide, lithium hydroxide, sodium carbonate, sodium bicarbonate, potassium carbonate, potassium bicarbonate, lithium carbonate, potassium phosphate, sodium phosphate, triethylamine, diisopropylethylamine, N,N-dimethylaniline, N,N-diethylaniline, pyridine, and mixtures thereof. Most preferably, base (B5) is sodium carbonate.

The reaction of a compound of Formula (8) and a compound of Formula (9) is conducted in the presence of a solvent (S7). Preferably, the solvent (S7) is selected from the group consisting of N-methyl-2-pyrolidone, N,N-dimethylacetamide, N,N-dimethylformamide, dimethyl sulfoxide, acetonitrile, tetrahydrofuran, toluene, dioxane, acetone, methyl isobutyl ketone, methyl t-butyl ether, dichloromethane and water. Most preferably, solvent (S7) is water.

The reaction of a compound of Formula (8) and a compound of Formula (9) is conducted at any suitable temperature. Preferably, the temperature is in the range of about 40° C. to about 80° C., more preferably between about 50° C. and about 70° C.

If required, hydrolysis of the intermediate compound of Formula (13) to form Lesinurad (1) is performed using any suitable means of hydrolysis. Preferably hydrolysis is conducted in the presence of a suitable acid or a base (B6). Suitable acids include aqueous solutions of trifluoroacetic acid, aqueous solutions of mineral acids such as hydrogen chloride, hydrogen bromide and sulfuric acid and aqueous solutions of sulfonic acids such as methane sulfonic acid and toluene sulfonic acid.

Suitable bases (B6) include, for example, tertiary amines, metal carbonates, metal bicarbonates and metal hydroxides. The base (B6) is preferably selected from the group consisting of sodium hydroxide, potassium hydroxide, lithium hydroxide, sodium carbonate, sodium bicarbonate, potassium carbonate, potassium bicarbonate, lithium carbonate, potassium phosphate, sodium phosphate, triethylamine, diisopropylethylamine, N,N-dimethylaniline, N,N-diethylaniline, pyridine, and mixtures thereof. More preferably, the base (B6) is an alkali metal hydroxide selected from lithium hydroxide, sodium hydroxide and potassium hydroxide. Most preferably, base (B6) is lithium hydroxide.

Hydrolysis of the compound of Formula (13) to form Lesinurad (1) is conducted in the presence of a solvent (S8). While any suitable solvent may be used, solvent (S8) is preferably selected from the group consisting of water and ethers such as dioxane and tetrahydrofuran (THF). Most preferably solvent (S8) is tetrahydrofuran.

Removal of $R^2$ may be conducted at any suitable temperature. Preferably, the temperature is in the range of about 0° C. to about 30° C., more preferably between about 0° C. and about 25° C.

In another embodiment of the present invention, there is provided a compound of Formula (11):

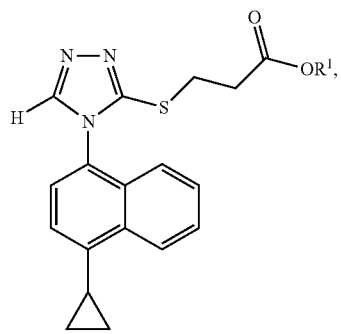

(11)

wherein $R^1$ is as defined above.

In another embodiment of the present invention, there is provided a compound of Formula (10):

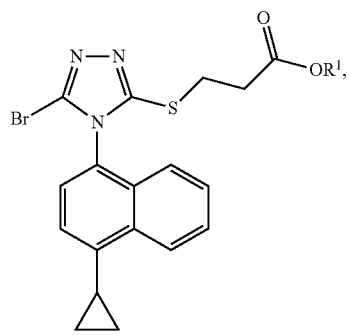

(10)

wherein $R^1$ is as defined above, with the proviso that R is not ethyl.

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Example 1: Preparation of Lesinurad (1) Using Ethylene Glycol as the Polyol Protecting Group a. Preparation of ethane-1,2-diyl bis({[4-(4-cyclopropylnaphthalen-1-yl)-4H-1,2,4-triazol-3-yl]sulfanyl}acetate) (Compound of Formula (3-A))

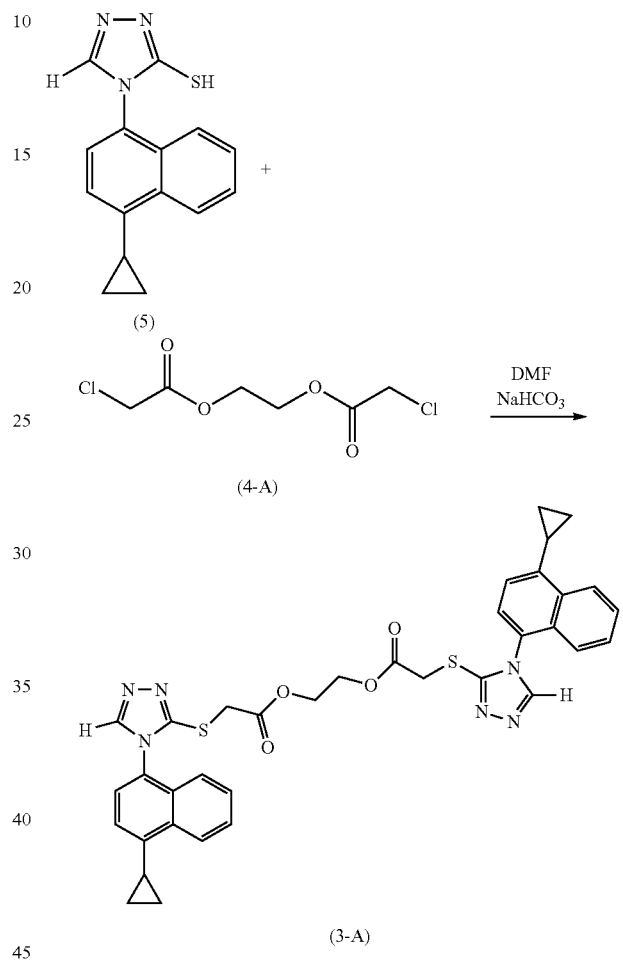

To a solution of the compound of Formula (5) (30 g, 112.22 mmol) in N,N-dimethylformamide (94 mL) was charged sodium bicarbonate (18.39 g, 218.96 mmol) to provide a suspension. 1,2-Bis(chloroacetoxy)ethane (compound of Formula (4-A)) (11.77 g, 54.74 mmol) was then charged and the mixture stirred at room temperature for 72 hours. Following the completion of the reaction, the reaction mixture was poured into ice water (250 mL) over 10 minutes to form a slurry, which was warmed to room temperature and stirred for 1 hour. The product was then collected by filtration, washed with cold (0-5° C.) water (2×60 mL), and suction dried for 45 minutes to provide a damp cake. A new flask was charged with the damp cake along with dichloromethane (300 mL) and stirred at room temperature for 30 minutes to afford a clear, biphasic solution. The organic phase was removed and washed with water (2×120 mL), dried over anhydrous sodium sulfate, and concentrated in vacuo at 30-35° C. The foamy solid was then dried in vacuo at room temperature for 24 hours to afford the compound of Formula (3-A) as a foamy light yellow solid (quantitative yield, HPLC purity=99.35 area %).

¹H-NMR (CDCl₃, 300 MHz) δ: 0.75-0.94 (4H, m), 1.10-1.22 (4H, m), 2.41 (2H, tt, J=5.64 Hz, 8.47 Hz), 4.08 (AB$_q$, 4H, Δδ$_{AB}$=0.05, J$_{AB}$=16.36 Hz), 4.34 (4H, s), 7.29-7.43 (6H, m), 7.57 (2H, apparent dt, J=1.23 Hz, 7.64 Hz), 7.66 (2H, apparent dt, J=1.23 Hz, 7.60 Hz), 8.28 (2H, s), 8.53 (2H, d, J=8.35 Hz).
b. Preparation of Lesinurad Nicotinamide Co-Crystal
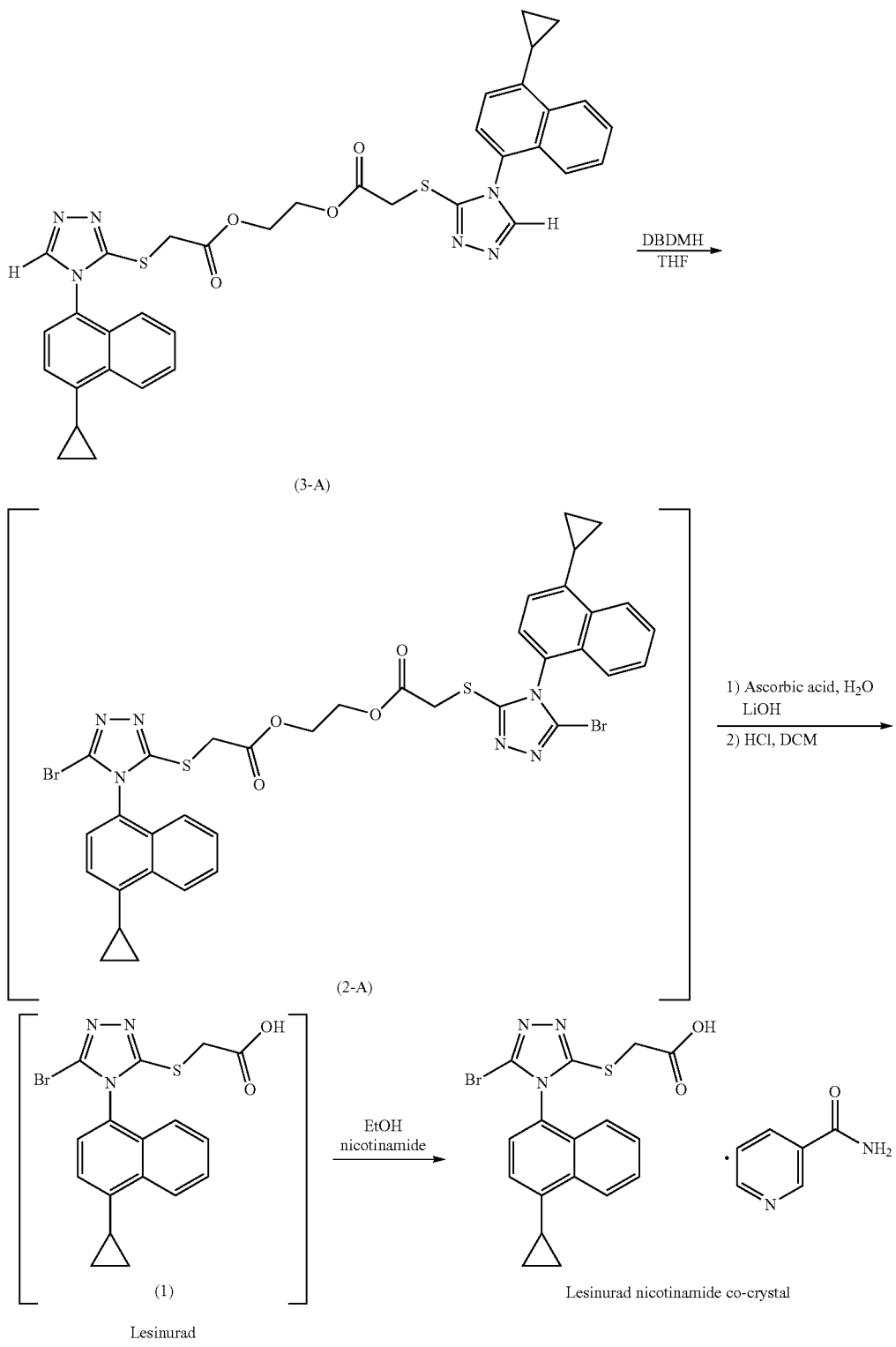

A flask containing a clear yellow solution of the compound of Formula (3-A) (35 g, 51.71 mmol) in tetrahydrofuran (245 mL) was wrapped in aluminum foil to exclude light and then heated to 30° C. 1,3-Dibromo-5,5-dimethylhydantoin (DBDMH) (22.18 g, 77.57 mmol) was charged in 5 portions over 10 minutes and the reaction was stirred at 30° C. for 4.5 hours and monitored by HPLC. Following the completion of the bromination to afford the compound of Formula (2-A), the reaction solution was cooled to room temperature and an aqueous solution of ascorbic acid (19.13 g, 108.60 mmol in 88 mL water) was added.

$^1$H-NMR compound of Formula (2-A) (CDCl$_3$, 300 MHz) δ: 0.81-0.94 (4H, m), 1.13-1.22 (4H, m), 2.43 (2H, tt, J=5.79 Hz, 8.47 Hz), 4.03 (AB$_q$, 4H, Δδ$_{AB}$=0.04, J$_{AB}$=16.41 Hz), 4.34 (4H, s), 7.24 (2H, apparent d, J=8.89 Hz), 7.36 (4H, d, J=2.85 Hz), 7.54-7.62 (2H, m), 7.63-7.70 (2H, m), 8.54 (2H, d, J=8.16 Hz).

The solution of the compound of Formula (2-A) was cooled to 5-10° C. and lithium hydroxide (14.86 g, 620.56 mmol) was added in portions, keeping the internal temperature of the solution below 20° C., to afford the intermediate lithium salt of Lesinurad (1). After 1 hour, the reaction was deemed complete by direct TLC (thin layer chromatography) of the reaction mixture (100% ethyl acetate).

Water (175 mL) was charged to the lithium salt and the tetrahydrofuran was removed in vacuo at 30-35° C. The reaction solution was cooled to room temperature, washed with ethyl acetate (2×175 mL), and the aqueous phase was acidified to pH 2-3 using 4 wt % hydrochloric acid (350 mL, 390.93 mmol). Dichloromethane (280 mL) was charged to the flask and the mixture was stirred at room temperature for 15 minutes. The organic and aqueous layers were then separated and the organic phase was washed with brine solution (175 mL). An emulsion formed during the wash but with time (1.25 hours), a clean separation of the aqueous and organic layers was attained. The organic phase was dried over anhydrous sodium sulfate and a $^1$H-NMR sample was taken using 1,4-dimethoxybenzene as an internal standard to determine the amount of Lesinurad (1) in solution (40.31 g, 99.71 mmol). This assay was used to determine the amount of nicotinamide used in the subsequent step.

The reaction solution was concentrated in vacuo at 30-35° C. to 2 volumes (81 mL). Ethanol (363 mL) was charged to the flask and the reaction solution was again concentrated in vacuo at 30-35° C. to 2 volumes (81 mL). Ethanol (322 mL) and nicotinamide (13.67 g, 111.93 mmol, 1.1 equivalents based on the above assay) were charged to the flask and stirred at room temperature whereupon a thin suspension was formed. The reaction was heated to 72-77° C. for 4 hours, slowly cooled to room temperature over 4 hours, and then stirred at room temperature for 8 hours. The reaction was then further cooled to 0-5° C. for 4 hours, following which the product was collected by filtration, washed with cold (0-5° C.) ethanol (40 mL) and cold (0-5° C.) acetone (40 mL), and dried in vacuo at 35-40° C. for 16 hours to afford a Lesinurad nicotinamide co-crystal as an off-white solid (42.10 g; 77% yield from the compound of Formula (3-A)).

$^1$H-NMR (d$_6$-DMSO) δ=0.82-0.92 (m, 2H), 1.10-1.20 (m, 2H), 2.48-2.62 (m, 1H, overlapping with DMSO peak), 4.01 (s, 2H), 7.17 (d, 1H, J=8.3 Hz), 7.40-7.55 (m, 2H), 7.57-7.80 (m, 4H), 8.12-8.26 (m, 2H), 8.59 (d, 1H, J=8.4 Hz), 8.71 (d, 1H, J=4.7 Hz), 9.05 (s, 1H), 13.01 (br s, 1H) ppm.

Although Lesinurad (1) was isolated as a nicotinamide co-crystal in the present example, it should be understood that Lesinurad (1) could alternatively be isolated in any other form desired, if preferred.

Example 2: Preparation of Lesinurad Nicotinamide Co-Crystal Using Ethylene Glycol as the Polyol Protecting Group A mixture of the compound of Formula (5) (3.00 g, 11.22 mmol), N,N-dimethylformamide (9.5 mL), sodium bicarbonate (1.84 g, 21.88 mmol) and the compound of Formula (4-A) (1.18 g, 5.47 mmol) was stirred at room temperature for 22.5 hours. A sample from the reaction mixture was analyzed by HPLC to confirm completion of the reaction (Compound of Formula (3-A)=95.75 area %, compound of Formula (5)=0.77 area %). Ice-water (0-5° C., 25 mL) was charged slowly into the reaction which caused the product to precipitate. The suspension was stirred at room temperature for 1.5 hours before filtration and washing with cold (0-5° C.) water (2×6 mL) to provide the compound of Formula (3-A) as damp solid. The damp solid (8.33 g) was dissolved in dichloromethane (60 mL), and the aqueous phase was removed (3.3 mL). The organic phase was washed with water (12 mL) and brine (12 mL) before being filtered through anhydrous sodium sulfate that was then washed with tetrahydrofuran (2×10 mL). The resulting solution was concentrated to 10 mL, and tetrahydrofuran (20 mL) was charged. After repeating this process, the solution was concentrated to 10 mL. $^1$H-NMR analysis of the concentrated THF solution showed negligible dichloromethane (molar ratio 1:0.11:0.07—THF:DCM:DMF).

The solution of compound of Formula (3-A) was diluted with tetrahydrofuran (20 mL), wrapped in aluminum foil to exclude light and heated to 30° C. 1,3-Dibromo-5,5-dimethylhydantoin (2.38 g, 8.21 mmol) was charged in portions and the reaction monitored by HPLC. Upon reaction completion after 3.3 hours, the mixture containing the compound of Formula (2-A) was cooled to room temperature, and an aqueous solution of L-ascorbic acid (2.02 g, 11.49 mmol in 9.2 mL water) was charged, which caused a slight exotherm of 4° C.

To the light orange solution of the compound of Formula (2-A) in L-ascorbic acid at 0-5° C. was charged lithium hydroxide (1.57 g, 65.64 mmol), at which point the solution became dark red. Direct TLC (100% ethyl acetate) of the reaction mixture after 25 minutes showed that the reaction was complete. Water (19 mL) was charged and the tetrahydrofuran was removed under reduced pressure. The resulting aqueous phase was washed with ethyl acetate (2×19 mL), and the aqueous phase was acidified with 4 wt % hydrochloric acid to pH 2-3. Dichloromethane (30 mL) was charged and the organic and aqueous phases were separated. The organic phase was washed with brine (23 mL) and dried over anhydrous sodium sulfate. $^1$H-NMR analysis of a sample of the organic phase was obtained with dimethoxy benzene as an internal standard to determine the amount of Lesinurad (1) in solution (8.21 mmol, 3.32 g).

The solution of Lesinurad (1) was concentrated to 6.6 mL, diluted with ethanol (30 mL), and concentrated once again to 6.6 mL. Filtration through polyester filter paper was conducted to remove small amounts of dark solids identified in the solution. The solution was then diluted with ethanol (26.5 mL, total 9 volumes ethanol). Nicotinamide (1.10 g, 9.00 mmol, 1.1 equiv. excess based on the assay described above) was charged to the solution, which was heated to 75° C. for 4 hours before being slowly cooled to room temperature. The resulting suspension was further cooled to 0-5° C. for 4 hours, then filtered and washed with cold ethanol (3.3 mL) and cold acetone (3.3 mL) to provide an off white solid that was dried to yield 3.72 g Lesinurad nicotinamide co-crystal (3.72 g, 64% yield from the compound of Formula (4-A); HPLC purity=98.49 area %).

Example 3: Preparation of Lesinurad (1) Using Glycerol as the Polyol Protecting Group a. Preparation of propane-1,2,3-triyl tris(chloroacetate) (Compound of Formula (4-B))

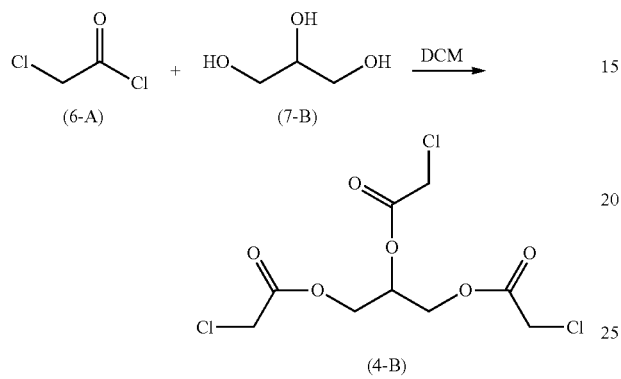

A flask was charged with glycerol (Compound of Formula (7-B)) (1.26 g, 13.72 mmol) and dichloromethane (5 mL) and was cooled to 5-10° C. and equipped with a basic scrubber containing a solution of aqueous sodium carbonate to quench the hydrochloric acid to be generated in the subsequent reaction. Chloroacetyl chloride (Compound of Formula (6-A)) (5 g, 44.27 mmol) was added and the reaction mixture was heated to 30-35° C. for 4 hours. An additional charge of the compound of Formula (6-A) (1.50 g, 13.28 mmol) was added and stirred for 18 hours at 30-35° C. at which point a mixture of products was observed by TLC. To the reaction was added dichloromethane (20 mL) and saturated aqueous sodium bicarbonate solution (20 mL). The organic layer was then separated, dried over anhydrous sodium sulfate, and concentrated in vacuo at 30-35° C. to afford a clear oil, which was then purified by column chromatography using heptanes and ethyl acetate to afford the compound of Formula (4-B) as a clear, colourless oil (2.16 g, 6.53 mmol; 49% yield from the compound of Formula (7-B)).

b. Preparation of propane-1,2,3-triyl tris({[4-(4-cyclopropylnaphthalen-1-yl)-4H-1,2,4-triazol-3-yl]sulfanyl}acetate) (Compound of Formula (3-B))

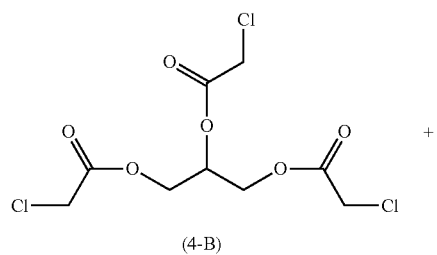

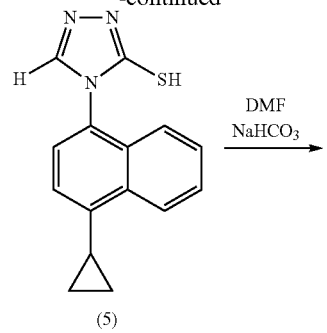

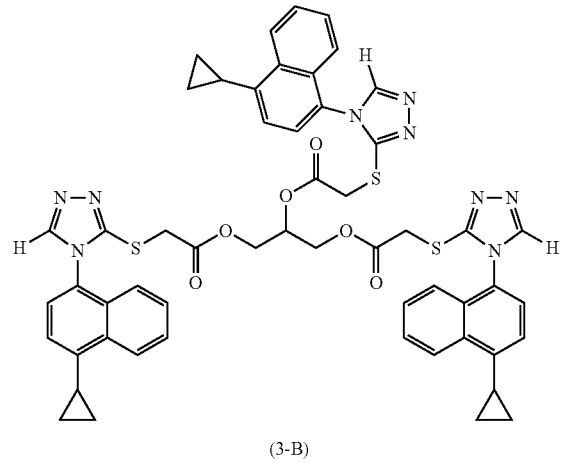

The compound of Formula (4-B) (2.1 g, 6.53 mmol), the compound of Formula (5) (5.33 g, 19.92 mmol), sodium bicarbonate (2.19 g, 26.12 mmol) and N,N-dimethylformamide (10 mL) were combined in a flask and the resulting suspension was stirred at room temperature for 6 days. The reaction mixture (containing ~18 mol % of the compound of Formula (5) by $^1$H-NMR) was then poured onto ice water (60 mL) over 10 minutes whereupon a suspension formed. The formed suspension was stirred for 30 minutes during which time the solution was warmed to room temperature. The solid product was then collected by filtration, washed with water (4×8 mL), and suction dried for 15 minutes to provide a damp cake. A new flask was charged with the damp cake along with dichloromethane (75 mL), and the mixture stirred at room temperature for 30 minutes to afford a biphasic solution. The organic phase was removed and washed with water (3×30 mL), dried over anhydrous sodium sulfate, and concentrated in vacuo at 30-35° C. to afford the compound of Formula (3-B) (5.78 g; 86% yield from the compound of Formula (4-B); HPLC purity=92 area %) as a light yellow foamy solid.

$^1$H-NMR (CDCl$_3$, 300 MHz) δ: 0.75-0.90 (6H, m), 1.15 (6H, d, J=8.50 Hz), 2.33-2.46 (3H, m), 3.96-4.20 (6H, m), 4.21-4.39 (4H, m), 5.27-5.36 (1H, m), 7.29-7.36 (6H, m), 7.36-7.43 (3H, m), 7.50-7.59 (3H, m), 7.59-7.68 (3H, m), 8.23 (1H, s), 8.25 (2H, s), 8.48-8.56 (3H, m).

c. Preparation of Lesinurad (1)

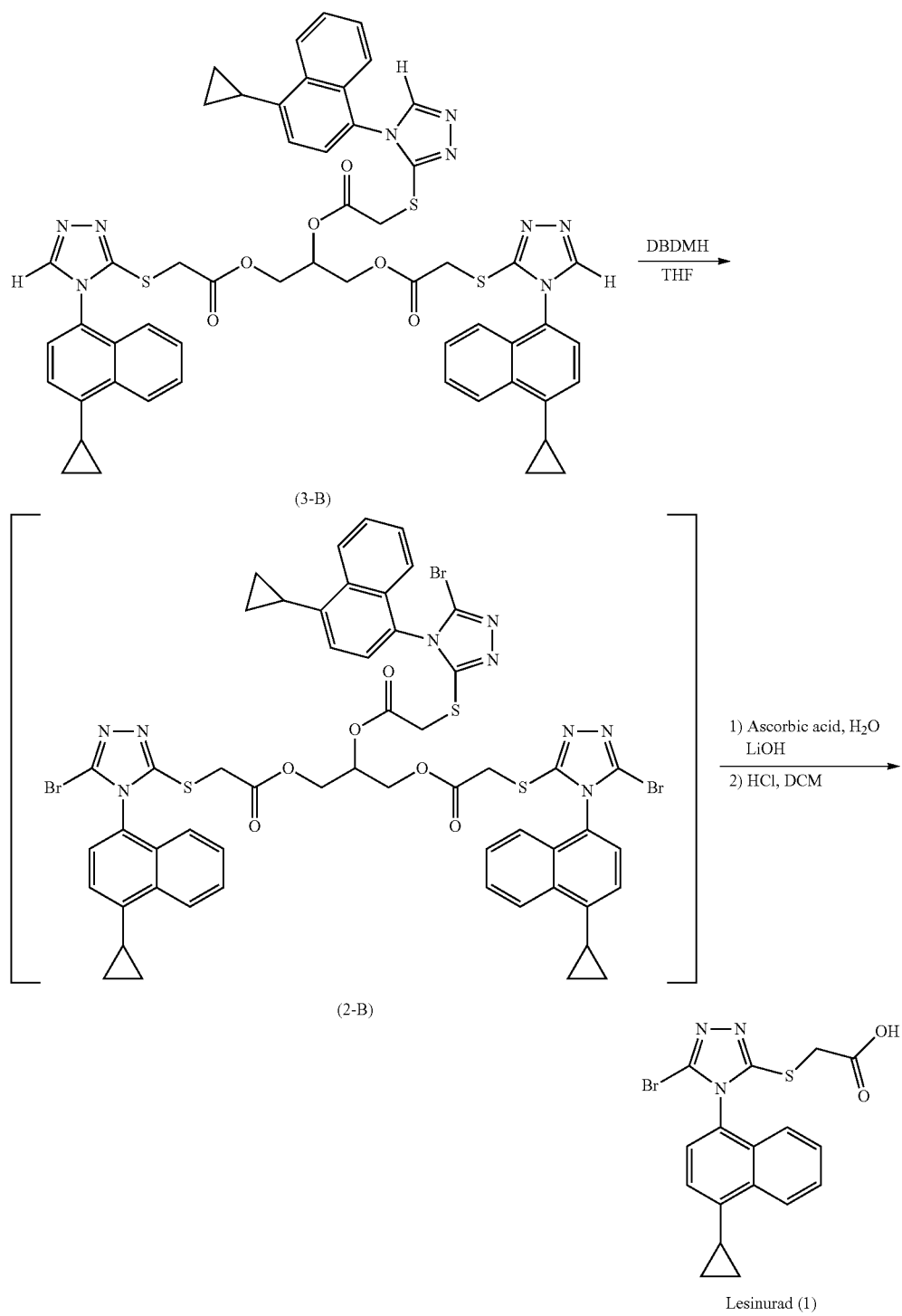

Lesinurad (1)

A flask containing a solution of the compound of Formula (3-B), 2 g, 1.97 mmol) in tetrahydrofuran (14 mL) was covered with foil to exclude light and heated to 30-35° C. 1,3-Dibromo-5,5-dimethylhydantoin (1.27 g, 4.44 mmol) was then added in 3 portions over 5 minutes, and stirred at 30-35° C. for 2 hours at which point the reaction was deemed complete by $^1$H NMR and TLC, and was quenched with aqueous ascorbic acid (1.04 g, 5.91 mmol in 5 mL water) to afford a solution containing compound (2-B).

$^1$H-NMR compound of Formula (2-B) (CDCl$_3$, 300 MHz) δ: 0.81-0.91 (6H, m), 1.12-1.20 (6H, m), 2.35-2.48 (3H, m), 3.93-4.13 (6H, m), 4.21-4.39 (4H, m), 5.28-5.37 (1H, m), 7.18-7.26 (3H, m), 7.31-7.38 (6H, m), 7.51-7.60 (3H, m), 7.61-7.70 (3H, m), 8.52 (1H, d, J=8.35 Hz), 8.53 (2H, d, J=8.35 Hz).

Lithium hydroxide (0.57 g, 23.64 mmol) was gradually charged to the mixture containing the compound of Formula (2-B) at room temperature in several portions to control the reaction temperature. After 2 hours, a second portion of lithium hydroxide (0.10 g, 3.94 mmol) was charged to the reaction to ensure basic conditions, following which the mixture was stirred at room temperature for 18 hours. After the hydrolysis was deemed complete by TLC, the tetrahydrofuran was removed in vacuo at 30-35° C. and the reaction was cooled to room temperature. Water (10 mL) was charged to the flask and the mixture was acidified to pH 2-3 using 4 wt % hydrochloric acid (14 mL, 15.63 mmol) to form a solution with a gummy precipitate. Dichloromethane (16 mL) was charged to the flask and stirred for 20 minutes. The resulting layers were separated and the organic phase was washed brine (10 mL) and dried over anhydrous sodium sulfate before being concentrated in vacuo at 30-35° C. to afford Lesinurad (1) as a foamy off-white solid (1.70 g; 30% yield from the compound of Formula (7-B); HPLC purity=93 area %).

Example 4: Preparation of Lesinurad (1) Using Ethylene Glycol as the Polyol Protecting Group a. Preparation of Polyethenyl Chloroacetate (Compound of Formula (4-C))

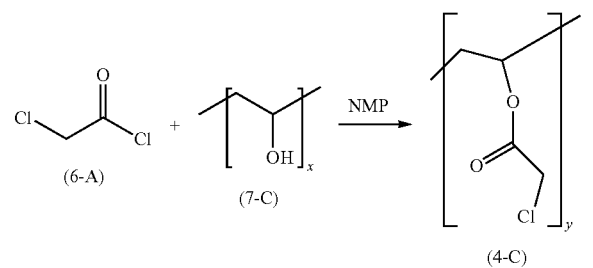

A flask containing poly(vinyl alcohol) having a molecular weight range of 31 000-50 000: 87-89% hydrolyzed (Compound of Formula (7-C)) (1 g, 17.92 mmol of free hydroxyl groups; MW 31 000-50 000=556-896 hydroxy monomers and 76-122 non-reactive acetate monomers; mean x=726 hydroxy monomers) and N-methyl-2-pyrrolidone (24 mL) was equipped with a basic scrubber containing a solution of aqueous sodium carbonate. The compound of Formula (6-A) (4.70 g, 41.62 mmol) was slowly added to control the reaction temperature, resulting in a light yellow thin suspension. The reaction was then heated to 45-50° C. for 22 hours before being cooled to room temperature and poured onto ice water (50 g) over 10 minutes to yield a large gummy ball. Dichloromethane (100 mL) was added and the mixture was stirred at room temperature for 30 minutes until a clear biphasic solution was obtained. The organic phase was removed and washed with a saturated aqueous sodium bicarbonate solution (24 mL), water (5×24 mL), and brine (24 mL), before being dried over anhydrous sodium sulfate and concentrated in vacuo at 30-35° C. to afford the compound of Formula (4-C) as a dark oil (2.01 g; ca. 15.20 mmol of chloroacetate substituents; mean y=618 monomers; 85% yield from the compound of Formula (7-C)).

b. Preparation of polyethenyl {[4-(4-cyclopropyl-naphthalen-1-yl)-4H-1,2,4-triazol-3-yl]sulfanyl}acetate (Compound of Formula (3-C))

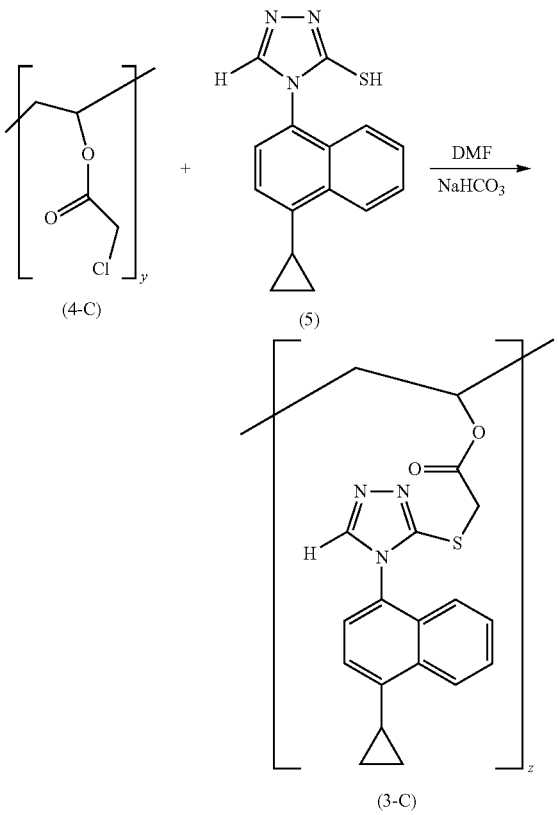

To the flask containing the compound of Formula (4-C) from step (a) (2.01 g; ca. 15.20 mmol of chloroacetate groups; mean y=618 monomers) was added the compound of Formula (5) (4.19 g, 15.69 mmol), sodium bicarbonate (5.02 g, 59.75 mmol), and N,N-dimethylformamide (16 mL). The mixture was stirred at room temperature for 44 hours, at which point there was approximately 6% of the compound of Formula (5) remaining by $^1$H-NMR. The reaction was then poured onto ice water (40 mL) over 10 minutes to provide a grey suspension that was stirred for 30 minutes while warming to room temperature. The suspension was then collected by filtration, washed with water (4 mL), and suction dried for 15 minutes to provide a damp cake. A new flask was charged with the damp cake along with dichloromethane (60 mL) and stirred at room temperature for 30 minutes to afford a biphasic solution. The organic phase was removed and washed with water (2×40 mL), dried over anhydrous sodium sulfate, and concentrated in vacuo at 30-35° C. to afford the compound of Formula (3-C) as a black glassy, foamy solid (5.28 g; ca. 14.52 mmol Lesinurad precursor substituents; mean z=593 monomers; 81% yield from the compound of Formula (7-C)).

$^1$H-NMR (CDCl$_3$, 300 MHz) δ: 0.69 (2H, broad peak), 1.02 (2H, broad peak), 1.78 (2H, broad peak), 2.25 (1H, broad peak), 3.89 (2H, broad peak), 4.83 (1H, broad peak), 7.21 (5H, broad peak), 8.07 (1H, broad peak), 8.36 (1H, broad peak).

c. Preparation of polyethenyl {[5-bromo-4-(4-cyclopropylnaphthalen-1-yl)-4H-1,2,4-triazol-3-yl]sulfanyl}acetate (Compound of Formula (2-C))

d. Preparation of Lesinurad (1)

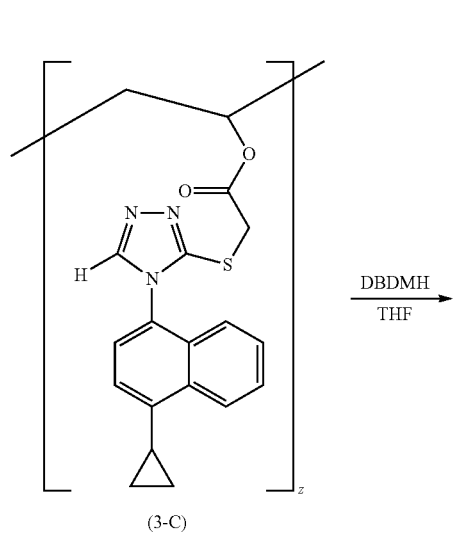

(3-C)

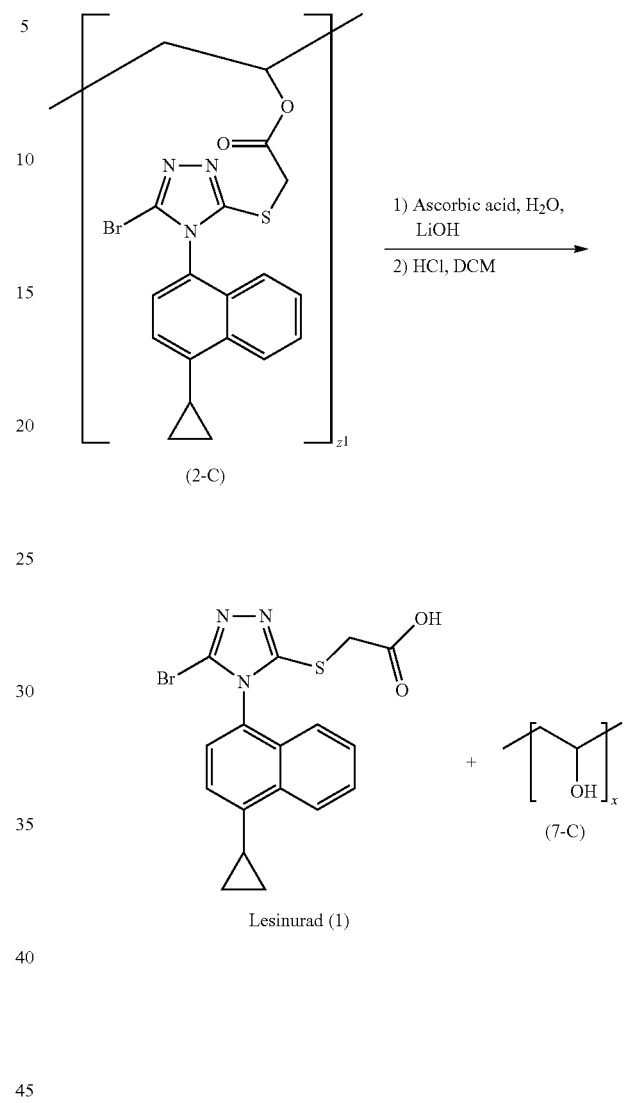

A flask containing the compound of Formula (3-C) (1 g; ca. 2.75 mmol Lesinurad precursor substituents; mean z=593 monomers) in tetrahydrofuran (7 mL) was covered with foil to protect from light and heated to 30-35° C. 1,3-Dibromo-5,5-dimethylhydantoin (0.54 g, 1.87 mmol) was then added in 3 portions over 5 minutes and stirred at 30-35° C. for 4 hours. After the reaction was deemed complete by $^1$H-NMR, the jelly-like mixture was quenched with aqueous L-ascorbic acid (0.92 g, 5.25 mmol in 5 mL water) to afford a solution of the compound of Formula (2-C).

$^1$H-NMR (CDCl$_3$, 300 MHz) δ: 0.68-0.78 (2H, m), 1.00-1.13 (2H, m), 1.58-2.02 (2H, broad peak), 2.36-2.51 (1H, m), 3.94-4.02 (1H, m), 4.26-4.39 (2H, m), 7.18-7.27 (1H, m), 7.38 (2H, d, J=2.73 Hz), 7.52-7.72 (2H, m), 8.55 (1H, d, J=7.86 Hz).

The solution of the compound of Formula (2-C) prepared in step (c) was cooled to 10-15° C. and lithium hydroxide (0.72 g, 30.00 mmol) was charged in several portions to control the reaction temperature. Following completion of the addition, the cooling bath was removed and the mixture was stirred at room temperature for 24 hours whereupon a thick dark red solution formed and the hydrolysis was deemed complete by TLC. The tetrahydrofuran was removed in vacuo at 30-35° C. and the reaction was cooled to room temperature. Water (10 mL) was charged to the flask and the reaction was acidified to pH 2-3 using 4 wt % hydrochloric acid (16 mL, 17.87 mmol) to form a yellow solution with a gummy precipitate. Dichloromethane (20 mL) was charged to the flask and the solution was stirred at room temperature for 40 minutes. The layers were separated and the organic phase was washed with water (2×20 mL) and brine (2×20 mL) before being dried over anhydrous sodium sulfate and concentrated in vacuo at 30-35° C. to afford 0.49 g of oil. The resulting oil was purified by column chromatography using ethyl acetate and methanol to afford Lesinurad (1) (0.24 g; 17.5% yield from the compound of Formula (7-C); HPLC purity=83.3 area %).

Example 5: Preparation of Lesinurad (1) Using a Methyl Propanoate Protecting Group a. Preparation of ethyl-3-[[4-(4-cyclopropyl-1-naphthalenyl)-4H-1,2,4-triazol-3-yl]thio]-propanoate (Compound of Formula (11-A))

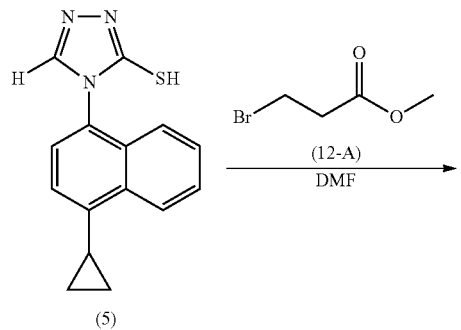

b. Preparation of ethyl-3-[[5-bromo-4-(4-cyclopropyl-1-naphthalenyl)-4H-1,2,4-triazol-3-yl]thio]-propanoate (Compound of Formula (10-A))

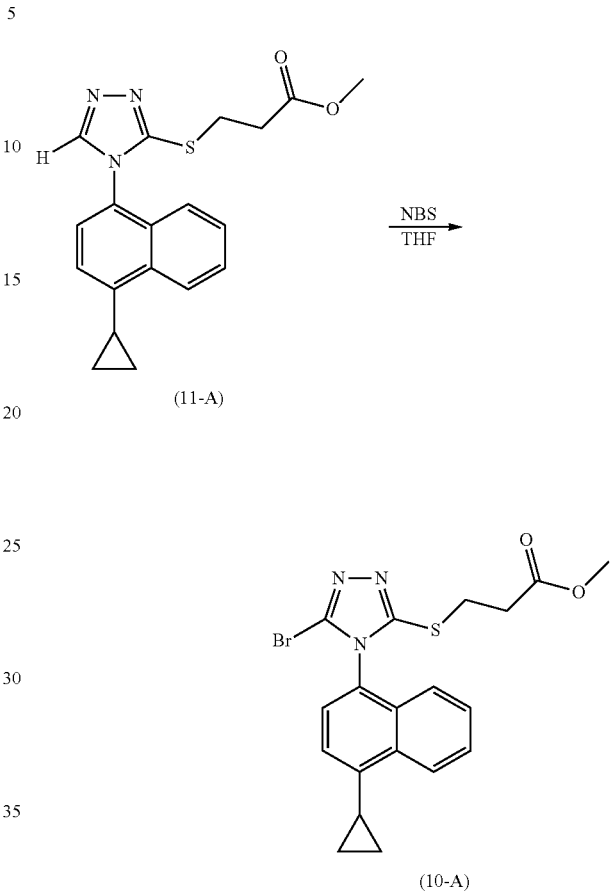

A pressure vessel containing the compound of Formula (5) (10 g, 37.40 mmol) and methyl 3-bromopropionate (7.73 g, 44.88 mmol) in N,N-dimethylformamide (70 mL) was sealed and heated to an external temperature of 60° C. for 3 days. The reaction was then cooled to room temperature to allow for a sample of the reaction mixture to be taken for $^1$H-NMR analysis (91% conversion). Methyl 3-bromopropionate (97%, 1.25 g, 7.48 mmol) was charged to the vessel and the reaction was re-sealed and heated to an external temperature of 60° C. for 24 hours. Following completion of the reaction, the reaction solution was concentrated in vacuo at 35-40° C. to remove the N,N-dimethylformamide. The resulting oil residue was then dissolved in dichloromethane (100 mL) and washed with a saturated aqueous sodium bicarbonate solution (50 mL), with the organic phase being dried over anhydrous sodium sulfate and concentrated in vacuo at 30-35° C. to afford a green oil (17.07 g). The oil was purified by silica gel column chromatography (column 27 cm×6 cm), using a gradient system of ethyl acetate and heptanes (2 L, 40:60 ethyl acetate:heptanes; 1 L, 50:50 ethyl acetate:heptanes; 2 L, ethyl acetate) to afford the compound of Formula (11) (9.75 g; 67% yield from the compound of Formula (5)) as a dark oil.

$^1$H-NMR (CDCl$_3$, 300 MHz) δ: 0.78-0.93 (2H, m), 1.12-1.21 (2H, m), 2.42 (1H, tt, J=5.44 Hz, 8.46 Hz), 2.91 (2H, t, J=6.77 Hz), 3.47 (2H, t, J=6.86 Hz), 3.64 (3H, s), 7.30 (1H, d, J=8.25 Hz), 7.35 (2H, s), 7.57 (1H, apparent dt, J=1.02 Hz, 8.22 Hz), 7.66 (1H, apparent dt, J=1.02 Hz, 8.04 Hz), 8.30 (1H, s), 8.54 (1H, d, J=8.44 Hz).

A flask was charged with the compound of Formula (11-A) (2 g, 5.66 mmol) and tetrahydrofuran (14 mL) and the solution was heated to 30° C., at which time N-bromosuccinimide (1.51 g, 8.49 mmol) was charged in portions over 10 minutes. Upon reaction completion after 4 hours (monitored by $^1$H-NMR), the reaction solution was cooled to 0-5° C. Cold toluene (0-5° C., 10 mL) and cold water (0-5° C., 10 mL) were charged to the reaction solution and the mixture stirred at 0-5° C. for 30 minutes. The organic phase was then washed with a 10% aqueous sodium thiosulfate solution (1×10 mL, 1×6 mL) and a saturated aqueous sodium bicarbonate solution (10 mL) before the organic phase was dried over anhydrous sodium sulfate and concentrated in vacuo at 30-35° C. to afford a yellow oil (2.46 g). The oil was purified by silica gel column chromatography (column 18 cm×3 cm) using ethyl acetate and heptanes (40:60) to afford the compound of Formula (10-A) (2.18 g; 89% yield from the compound of Formula (11-A)).

$^1$H-NMR (CDCl$_3$, 300 MHz) δ: 0.80-0.95 (2H, m), 1.10-1.23 (2H, m), 2.43 (1H, tt, J=5.46 Hz, 8.38 Hz), 2.88 (2H, t, J=6.72 Hz), 3.43, (2H, t, J=6.78 Hz), 3.64 (3H, s), 7.20 (1H, d, J=8.16), 7.29-7.40 (2H, m), 7.57 (1H apparent dt, J=1.14 Hz, 8.28 Hz), 7.66 (1H, apparent dt, J=1.05 Hz, 8.04 Hz), 8.54 (1H, d, J=8.38 Hz).

c. Preparation of ethyl-3-[[5-bromo-4-(4-cyclopropyl-1-naphthalenyl)-4H-1,2,4-triazol-3-yl]thio]-propanoate (Compound of Formula (9))

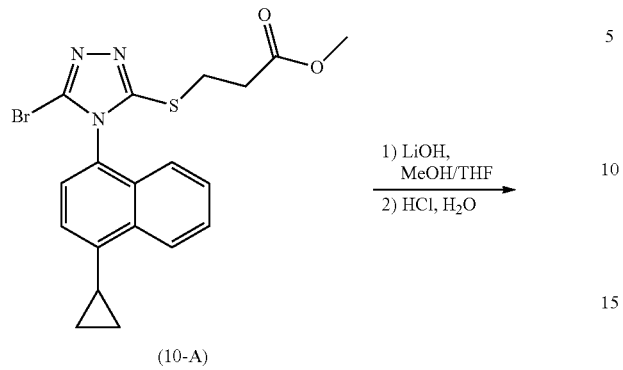

(10-A)

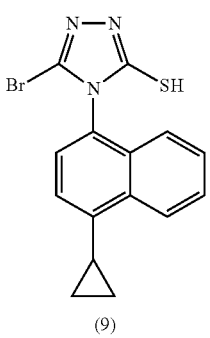

(9)

To a solution of the compound of Formula (10-A) (1.6 g, 3.70 g) in tetrahydrofuran (19 mL) and methanol (13 mL) was dropwise charged a 1 M lithium hydroxide aqueous solution (11.1 mL). After 2.5 hours of stirring at room temperature, the reaction was deemed complete by TLC (1:1 ethyl acetate:heptanes, starting material rf=0.56, product rf=0.66) and 2 wt % aqueous hydrochloric acid (27 g) was added over 5 minutes. The resulting solution was then concentrated in vacuo at 30-35° C. to remove the organic solvents and afford a white precipitate. Water (15 mL) was then charged to the flask to form a white suspension. Following stirring of the suspension at room temperature for 2 hours, the product was collected by filtration, washed with water (2×3 mL), and dried in vacuo at 35-40° C. to afford the compound of Formula (9) as a white solid (1.12 g; 87% yield from the compound of Formula (10-A)).

$^1$H-NMR (CDCl$_3$, 300 MHz) δ: 0.78-0.94 (2H, m), 1.05-1.23 (2H, m), 2.36-2.49 (1H, m), 7.37 (1H, d, J=8.38 Hz), 7.41 (2H, s), 7.54-7.7 (2H, m), 8.55 (1H, d, J=7.98 Hz), 11.50 (1H, Br S).

d. Preparation of Lesinurad (1)

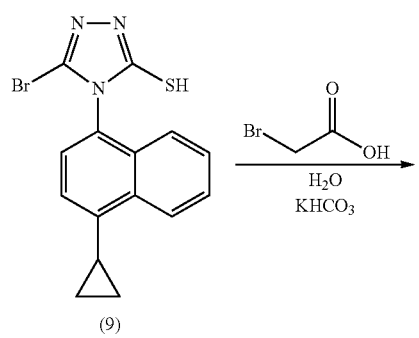

(9)

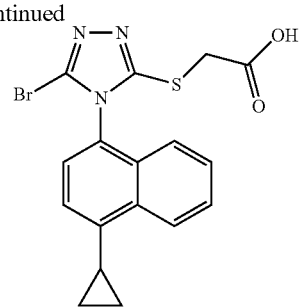

Lesinurad (1)

A flask was charged with the compound of Formula (9) (0.2 g, 0.58 mmol), water (1 mL), and potassium bicarbonate (0.06 g, 0.62 mmol) and the resulting white suspension was stirred at room temperature. Bromoacetic acid (0.09 g, 0.62 mmol) was charged to the reaction and a vigorous effervescence was observed. A second portion of potassium bicarbonate (0.06 g, 0.62 mmol) was then charged, and the reaction suspension was heated to 60° C. After 2 hours, a clear solution was observed and was then cooled to room temperature after confirming reaction completion by TLC (1:1 ethyl acetate:heptanes; starting material Rf=0.44, product Rf=baseline). The reaction mixture was acidified to a pH of 2-3 using 4 wt % hydrochloric acid whereupon a white precipitate was observed. The precipitate was collected by filtration, washed with water (2×0.4 mL), and dried in vacuo at 35-40° C. to afford Lesinurad (1) as a white solid (0.19 g; 80% yield from the compound of Formula (9).

What is claimed is:
1. A process for the preparation of Lesinurad (1):

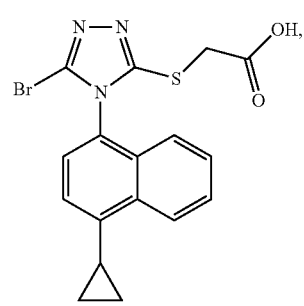

or a salt thereof, the process comprising hydrolysis, in the presence of a solvent (S3), of a compound of Formula (2):

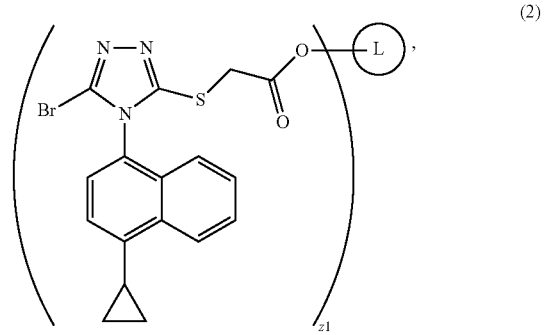

wherein
L is a linker corresponding with the backbone of either:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom; and
wherein the hydroxyl substituents of the polyol provide the oxygen atoms in the ester connection in the compound of Formula (2);
x and z1 are each at least 2; and
z1≤x.

2. The process of claim 1, wherein L is a linker corresponding with the backbone of a monomeric polyol selected from the group consisting of C2-C10 aliphatic diols, C3-C10 aliphatic triols, C4-C20 aliphatic tetrols, saccharides and sugar alcohols.

3. The process of claim 2, wherein the monomeric polyol is ethane-1,2-diol or propane-1,2,3-triol.

4. The process of claim 3, wherein the monomeric polyol is ethane-1,2-diol and x and z1 are both 2.

5. The process of claim 1, wherein the hydrolysis is conducted in the presence of a base (B2).

6. The process of claim 5, wherein the base (B2) is an alkali metal hydroxide.

7. The process of claim 6, wherein the base (B2) is lithium hydroxide.

8. The process of claim 1, wherein the solvent (S3) is selected from the group consisting of water and ethers.

9. The process of claim 3, wherein the compound of Formula (2) is prepared by a process comprising reacting, in the presence of a solvent (S2), a compound of Formula (3):

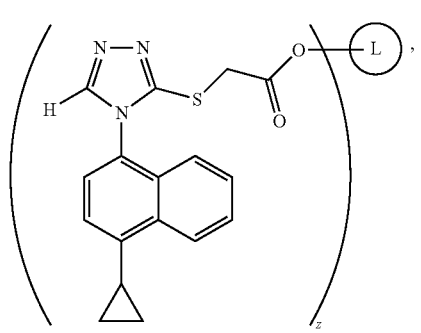

with a brominating agent,
wherein
L is a linker corresponding with the backbone of a monomeric polyol selected from the group consisting of ethane-1,2-diol and propane-1,2,3-triol; and
z is 2 or 3.

10. The process of claim 9, wherein the brominating agent is selected from the group consisting of 1,3-dibromo-5,5-dimethylhydantoin and N-bromosuccinimide.

11. The process of claim 10, wherein the brominating agent is 1,3-dibromo-5,5-dimethylhydantoin.

12. The process of claim 9, wherein the solvent (S2) is selected from the group consisting of acetonitrile, N,N-dimethylformamide, ethyl acetate, isopropyl acetate, methyl t-butyl ether, tetrahydrofuran, dioxane, dichloromethane, methanol, cyclohexane and hexane.

13. The process of claim 9, wherein the compound of Formula (2) is not isolated.

14. The process of claim 9, wherein the compound of Formula (3) is prepared by a process comprising reaction of a compound of Formula (5):

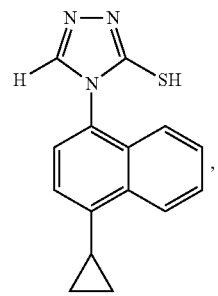

in the presence of a base (B1) and a solvent (S1), with a compound of Formula (4):

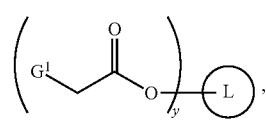

wherein
L is a linker corresponding with the backbone of a monomeric polyol selected from the group consisting of ethane-1,2-diol and propane-1,2,3-triol;
G¹ is a leaving group; and
y is 2 or 3.

15. The process of claim 14, wherein G¹ is a halide.

16. The process of claim 14, wherein the solvent (S1) is N,N-dimethylformamide.

17. A compound of Formula (3):

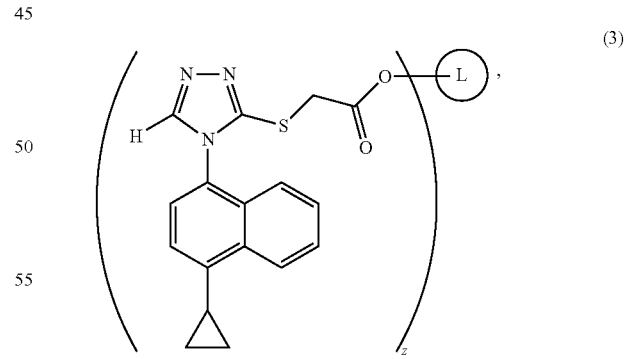

wherein
L is a linker corresponding with the backbone of a monomeric polyol selected from the group consisting of ethane-1,2-diol and propane-1,2,3-triol;
wherein the hydroxyl substituents of the polyol provide the oxygen atoms in the ester connection in the compound of Formula (3); and
z is 2 or 3.

18. A compound of Formula (2):

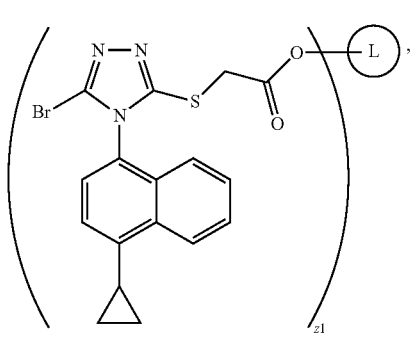

(2)

wherein
L is a linker corresponding with the backbone of either:
(a) a monomeric polyol having x hydroxyl substituents, each bonded to a different carbon atom;
(b) a water-soluble polymeric polyol having x mean hydroxyl substituents, each bonded to a different carbon atom; or
(c) a water-insoluble polymeric polyol suitable for use as a solid phase support having x mean hydroxyl substituents, each bonded to a different carbon atom; and wherein the hydroxyl substituents of the polyol provide the oxygen atoms in the ester connection in the compound of Formula (2);

x and z1 are each at least 2; and z1≤x.

19. The compound of claim 18, wherein L is a linker corresponding with the backbone of a monomeric polyol selected from the group consisting of C2-C10 aliphatic diols, C3-C10 aliphatic triols, C4-C20 aliphatic tetrols, saccharides and sugar alcohols.

20. The compound of claim 19, selected from:

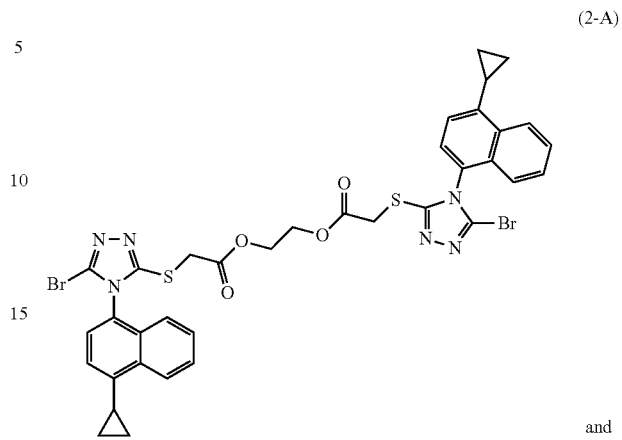

(2-A)

and

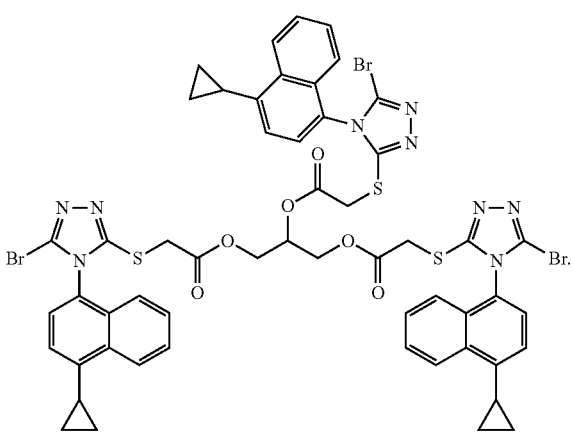

(2-B)

* * * * *